US012788897B2

(12) United States Patent
Ni et al.

(10) Patent No.: US 12,788,897 B2
(45) Date of Patent: Nov. 10, 2026

(54) AUTOMATIC SYRINGE

(71) Applicant: SHANDONG WEGO PREFILLS PHARMACEUTICAL PACKAGING CO., LTD, Weihai (CN)

(72) Inventors: Shili Ni, Weihai (CN); Xiaofeng Sun, Weihai (CN); Qianhe Xu, Weihai (CN); Wenzheng Li, Weihai (CN); Zhifei Li, Shandong (CN)

(73) Assignee: SHANDONG WEGO PREFILLS PHARMACEUTICAL PACKAGING CO., LTD, Weihai (CN)

( * ) Notice: Subject to any disclaimer, the term of this patent is extended or adjusted under 35 U.S.C. 154(b) by 773 days.

(21) Appl. No.: 18/032,160

(22) PCT Filed: May 24, 2021

(86) PCT No.: PCT/CN2021/095525
§ 371 (c)(1),
(2) Date: Apr. 14, 2023

(87) PCT Pub. No.: WO2022/077910
PCT Pub. Date: Apr. 21, 2022

(65) Prior Publication Data

US 2023/0390502 A1 Dec. 7, 2023

(30) Foreign Application Priority Data

Oct. 16, 2020 (CN) .......................... 202011110579.9
Oct. 16, 2020 (CN) .......................... 202022322096.7

(51) Int. Cl.
*A61M 5/32* (2006.01)
*A61M 5/20* (2006.01)
*A61M 5/24* (2006.01)

(52) U.S. Cl.
CPC ............ *A61M 5/3245* (2013.01); *A61M 5/20* (2013.01); *A61M 5/2033* (2013.01);
(Continued)

(58) Field of Classification Search
CPC .. A61M 5/20; A61M 5/2033; A61M 5/31571; A61M 5/326; A61M 5/31501;
(Continued)

(56) References Cited

U.S. PATENT DOCUMENTS 10,207,052 B2 2/2019 Saussaye
2007/0129686 A1 6/2007 Daily et al.
(Continued)

FOREIGN PATENT DOCUMENTS

CH 705992 A2 6/2013
CN 110573199 A 12/2019
(Continued)

OTHER PUBLICATIONS

The European Search Report issued on Apr. 23, 2025 for the European counterpart Divisional Application No. 25156842.4.
(Continued)

*Primary Examiner* — Michael J Tsai
*Assistant Examiner* — Forrest B Dipert
(74) *Attorney, Agent, or Firm* — Yue (Robert) Xu; Apex Attorneys at Law, LLP

(57) ABSTRACT

An automatic syringe, comprising: a housing, a needle guard cover, a push rod, a sounding cylinder, an inner tube, a release ring, a driving elastic member, and a resetting elastic member. During use, a needle cylinder is fixed in the housing; a needle head protrudes from the front of the housing; the needle guard cover is retractably attached to the housing; the needle guard cover can push the release ring to slide toward the rear end of the housing; after the release ring moves to the rear end, a first clip of the inner tube
(Continued)

releases the snap-fit position-limiting of the push rod; the push rod pushes a piston under the action of the driving elastic member to inject the liquid in the needle cylinder into a part of the body to be injected, achieving automatic injection.

19 Claims, 27 Drawing Sheets

(52) U.S. Cl.
CPC ... *A61M 5/3202* (2013.01); *A61M 2005/2013* (2013.01); *A61M 2005/2418* (2013.01); *A61M 2005/2437* (2013.01); *A61M 5/3204* (2013.01); *A61M 2005/3247* (2013.01); *A61M 2005/3267* (2013.01); *A61M 2205/581* (2013.01)

(58) Field of Classification Search
CPC .............. A61M 5/3202; A61M 5/3204; A61M 5/3245; A61M 5/31578; A61M 5/3158; A61M 2005/2073; A61M 2005/208; A61M 2005/2013; A61M 2005/2086; A61M 2005/2418; A61M 2005/2437
See application file for complete search history.

(56) References Cited

U.S. PATENT DOCUMENTS

| | | | |
|---|---|---|---|
| 2013/0096512 | A1 | 4/2013 | Ekman et al. |
| 2013/0274676 | A1 | 10/2013 | Ekman et al. |
| 2013/0324939 | A1 | 12/2013 | Brereton et al. |
| 2017/0007621 | A1 | 1/2017 | Wotton et al. |
| 2017/0136189 | A1 | 5/2017 | Tschirren et al. |
| 2017/0209647 | A1 | 7/2017 | Daniel |
| 2019/0374727 | A1 | 12/2019 | Dugand et al. |
| 2020/0139047 | A1 | 5/2020 | Hirschel et al. |
| 2020/0164138 | A1 | 5/2020 | Holmqvist |
| 2020/0238010 | A1 | 7/2020 | Dugand et al. |
| 2023/0008831 | A1 | 1/2023 | Huang et al. |

FOREIGN PATENT DOCUMENTS

| | | | | | |
|---|---|---|---|---|---|
| CN | 111150906 | A | | 5/2020 | |
| CN | 112076364 | A | | 12/2020 | |
| CN | 212914096 | U | | 4/2021 | |
| WO | WO-2011043714 | A1 | * | 4/2011 | .......... A61M 5/2033 |
| WO | WO-2011123024 | A1 | * | 10/2011 | .............. A61M 5/20 |
| WO | WO-2013016832 | A1 | * | 2/2013 | .......... A61M 5/2033 |
| WO | WO-2013178512 | A1 | * | 12/2013 | .......... A61M 5/2033 |
| WO | WO-2014154490 | A2 | * | 10/2014 | ........ A61M 5/31571 |
| WO | 2020173997 | A1 | | 9/2020 | |

OTHER PUBLICATIONS

The European Search Report issued on Apr. 23, 2025 for the European counterpart Divisional Application No. 25156845.7.
The European Search Report issued on Apr. 23, 2025 for the European counterpart Divisional Application No. 25156849.9.
International Search Report for PCT/CN2021/095525 mailed Aug. 11, 2021, ISA/CN.
Search Report dated Mar. 26, 2024 for European patent application No. 21878964.2.

* cited by examiner

AUTOMATIC SYRINGE

This application is the national phase of International Patent Application No. PCT/CN2021/095525, titled "AUTOMATIC SYRINGE", filed on May 24, 2021.

This application claims the benefit of priority to Chinese Patent Application No. 202011110579.9, titled "AUTOMATIC SYRINGE", filed with the China National Intellectual Property Administration on Oct. 16, 2020, which is incorporated herein by reference in its entirety.

This application also claims the benefit of priority to Chinese Patent Application No. 202022322096.7, titled "AUTOMATIC SYRINGE", filed with the China National Intellectual Property Administration on Oct. 16, 2020, which is incorporated herein by reference in its entirety.

FIELD

The present application relates to the technical field of medical instruments, and in particular, to an automatic syringe.

BACKGROUND

An automatic syringe is a medical instrument which can automatically inject a liquid drug in a pre-filled syringe into a patient's body and can meet the requirements of self-drug-injection for the user. The automatic syringe is a medical instrument for use by the patient himself Because ordinary patients are not professional medical staffs, the automatic syringe is generally required to be simple and easy to use, and have high reliability and comfortable experience, and it is also required to send a prompt signal after the injection is complete to prompt the user to confirm the completion of injection.

During use of a conventional automatic syringe, puncture and injection are generally achieved by simply pressing a front end of the syringe against the part to be injected and holding a rear end of the syringe by hand to move. When the front end of the automatic syringe is positioned at the injection site of the patient, a starting component on the automatic syringe is pressed to activate the automatic syringe, so that the needle can quickly puncture the skin, and the drug is automatically injected through the needle.

However, the conventional automatic syringe has a complicated structure and a large number of internal parts, and therefore is easy to fail and has poor product reliability. Further, it takes excessive processing and assembling steps to manufacture the product, which makes the product cost higher.

Therefore, how to improve the reliability of the automatic syringe is a major concern of those skilled in the art at present.

SUMMARY

In view of this, it is an object of the present application to provide an automatic syringe, which has the advantages of simple structure, high reliability, easy assembly and low cost.

To achieve the above object, the following technical solutions are provided according to the present application.

An automatic syringe includes a housing, a needle guard cover, a push rod, a prompting cylinder, an inner tube, a release ring, a driving elastic member and a resetting elastic member.

A syringe fixing structure for fixing a syringe is arranged in the housing. An opening for a needle to extend out is arranged at a front end of the housing.

The release ring and the needle guard cover are sequentially and slidably arranged on an inner side of the housing from a rear end to the front end of the housing. The needle guard cover can extend out of the front end of the housing and slide towards the rear end relative to the housing to push the release ring. The resetting elastic member is configured to act on the release ring and drive the release ring to push the needle guard cover to slide towards the front end of the housing. The housing is provided with a needle-guard-cover limiting structure for limiting a forward sliding distance of the needle guard cover relative to the housing.

The push rod is slidably arranged in the housing along an axial direction. A front end of the push rod is used for pushing a piston in the syringe. The driving elastic member is configured to act on the push rod and drive the push rod to slide towards a front end of the syringe. A push-rod limiting structure is arranged on an outer circumference of the push rod.

The prompting cylinder is slidably sleeved on the outer circumference of the push rod along the axial direction. The driving elastic member is configured to act on the prompting cylinder and drive the prompting cylinder to slide towards a rear end of the housing. The prompting cylinder is provided with a push-rod-limiting cooperating structure. A prompting-cylinder limiting structure is arranged between the prompting cylinder and the inner tube.

The inner tube is fixed inside the housing and sleeved on an outer circumference of the prompting cylinder. The release ring is slidably sleeved on an outer circumference of the inner tube. The inner tube is provided with a first clip capable of elastically moving along a radial direction, and the first clip is deviated radially outward under its own elastic force.

The first clip can be deviated radially inward under limiting from an inner wall of the release ring, and the first clip is snap-fitted and position-limited with the push-rod limiting structure through the push-rod-limiting cooperating structure. Under the support of an outer wall of the push rod, the prompting-cylinder limiting structure can limit the sliding of the prompting cylinder relative to the inner tube. After the push rod has slid towards the front end for a preset distance, the prompting-cylinder limiting structure is no longer supported by the push rod.

Preferably, a signal structure is arranged at the rear end of the housing and used for colliding and position-limiting with the prompting cylinder.

Preferably, the signal structure is an end plate fixed at the rear end of the housing.

In an embodiment, the automatic syringe further includes a needle cap detachably connected to a front end of the needle guard cover.

Preferably, a rear end of the needle cap is provided with a claw for catching a rear end of a needle sheath, and the claw can exert a pulling force on the needle sheath towards the front end.

Preferably, an anti-dropping recess-protrusion engaging structure is arranged between an inner ring of the needle cap and a circumference of the needle guard cover.

Preferably, a needle-cap limiting structure is arranged between the housing and the needle cap, which is used to limit the movement of the needle cap towards the rear end relative to the housing.

Preferably, the syringe fixing structure is a syringe fixing cylinder fixed on the inner side of the housing, and a front end of the syringe fixing cylinder is provided with a syringe clamping claw for position-limiting and cooperating with a front shoulder of the syringe.

Preferably, a rear end of the syringe fixing cylinder is provided with a support body for position-limiting and cooperating with a rear end flange of the syringe, and an elastic cushion block is arranged between the support body and a front end face of the rear end flange of the syringe.

Preferably, a front end of the inner tube abuts against a rear end face of the rear end flange of the syringe, and a rear end of the inner tube abuts against the rear end of the housing.

Preferably, the rear end of the housing is provided with an annular protrusion coaxially cooperating with the rear end of the inner tube, and a rotation limiting structure for preventing the inner tube from rotating is arranged between a side wall of the housing and the inner tube.

Preferably, the push-rod-limiting cooperating structure is a prompting-cylinder avoidance notch defined in a side wall of the prompting cylinder, and the prompting-cylinder avoidance notch extends along an axial direction of the prompting cylinder.

Preferably, the prompting-cylinder limiting structure includes a prompting-cylinder protrusion arranged on an outer wall of the prompting cylinder, and an inner-tube clamping hole defined in the inner tube for clamping and limiting the prompting-cylinder protrusion.

Preferably, the inner tube is provided with an inner-tube avoidance slot hole extending along the axial direction, where the release ring is provided with a second clip which is in sliding fit with the inner-tube avoidance slot hole and can interact with the prompting cylinder, and an outer side of the prompting cylinder is provided with a clip limiting structure used for limiting the movement of the second clip towards the rear end of the housing.

Preferably, the push rod is of a hollow rod-shaped structure, and the driving elastic member is a push rod spring arranged inside the push rod, wherein the push rod spring is compressed between a front end of the push rod and a rear end of the prompting cylinder.

Preferably, a spring guide rod is slidably arranged in the push rod, and the push rod spring is sleeved on an outer circumference of the spring guide rod.

Preferably, the resetting elastic member is a reset spring compressed between the release ring and the housing.

Preferably, the housing includes a front housing and a rear housing, where the front housing is connected to a front end of the rear housing.

Preferably, the housing and the needle guard cover are each provided with an observation window extending along the axial direction.

Preferably, the needle-guard-cover limiting structure includes a first limiting step arranged on an inner wall of the housing and a second limiting step arranged on an outer wall of the needle guard cover.

The working principle of the automatic syringe provided by the present application is as follows:

A pre-filled syringe can be mounted and fixed in the housing of the automatic syringe in advance. The needle is directed towards a front opening of the housing and is protected by the needle sheath. In an initial assembly state before injection, the needle guard cover is extended out of the front end of the housing to protect the needle and the needle sheath.

When injection is needed, the needle sheath protecting the needle is removed, then the housing is held by hand with the front end of the housing being aligned with the part of the body to be injected, and the needle guard cover is aligned with the part to be injected and is pressed firmly. At this time, the needle guard cover overcomes the elastic force of the resetting elastic member and drives the release ring to move together towards the rear end relative to the housing, so that the needle can pierce into the part to be injected. During the movement of the release ring towards the rear end of the housing, the first clip of the inner tube disengages from the limitation of the inner wall of the release ring, thus no longer snap-fitting and limiting the push rod. Then, the push rod slides towards the front end of the syringe under the action of the driving elastic member, and injects, by pushing the piston, the liquid in the syringe into the body through the needle, thus achieving automatic injection.

In the injection by the push rod, the outer wall of the push rod can provide continuous support for the prompting-cylinder limiting structure, thereby ensuring that the positions of the prompting cylinder and the inner tube are relatively fixed. After the push rod has slid for a preset distance, that is, after the push rod has injected a preset amount of liquid in the syringe into the body, the prompting-cylinder limiting structure is no longer supported by the outer wall of the push rod, so that the prompting cylinder can slide towards the rear end of the housing under the action of the driving elastic member. In the process of sliding or after sliding for a certain distance, the prompting cylinder can remind the user that the injection is complete in various ways, such as sounding, lighting, impact, and vibration. The user only needs to pull the needle out of the body to complete the whole injection process.

The technical solution of the present application has the following beneficial effects.

1) The automatic syringe provided in this solution can achieve the automatic injection function of the pre-filled syringe through eight components. As compared with the automatic syringe in the conventional technology, the automatic syringe in this solution has a simple structure and fewer parts.
2) In this solution, the automatic injection function can be achieved just by pressing. The mechanism has a simple operation principle and high reliability.
3) The product is easy to assemble, thus reducing the manual assembly cost and improving the product yield.

BRIEF DESCRIPTION OF THE DRAWINGS

For more clearly illustrating the technical solutions in the embodiments of the present application or in the conventional technology, drawings referred to for describing the embodiments or the conventional technology will be briefly described hereinafter. Apparently, the drawings in the following description are only several examples of the present application, and for those skilled in the art, other drawings may be obtained based on these drawings without any creative efforts.

Figure 1:
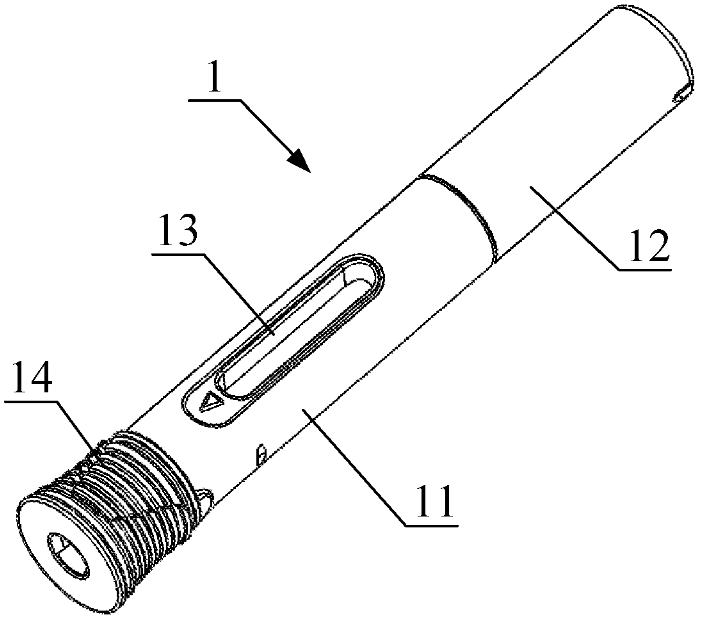
FIG. 1 is a schematic diagram of an overall external structure of an automatic syringe in a specific embodiment of the present application.

Reference numerals in FIGS. 1 to 41 are listed as follows:

1 housing, 11 front housing, 12 rear housing, 13 observation window, 110 syringe fixing cylinder, 111 first limiting step, 112 syringe clamping claw, 113 elastic cushion block, 114 support body, 120 end plate, 121 annular protrusion, 122 inner-tube anti-rotation limiting groove, 123 rear-housing mounting ring groove;

14 needle cap, 141 needle-sheath mounting hole, 142 needle-cap anti-dropping limiting part, 143 claw, 144 needle-cap limiting structure, 145 needle-cap inner cylinder;

2 needle guard cover, 21 needle-guard-cover anti-dropping limiting part, 22 second limiting step, 23 needle-guard-cover inner ring protrusion;

3 push rod, 31 push-rod ring groove;

4 prompting cylinder, 41 prompting-cylinder protrusion, 42 prompting-cylinder avoidance notch, 43 clip limiting opening, 44 clip avoidance opening;

5 inner tube, 51 inner-tube anti-rotation protrusion, 52 inner-tube front end, 53 inner-tube clamping hole, 54 inner-tube avoidance slot hole, 55 first clip;

6 release ring, 61 release-ring rear end flange, 62 second clip;

7 push rod spring, 71 spring guide rod, 711 guide rod end;
8 reset spring;
9 syringe, 91 needle, 92 needle sheath, 93 piston, 94 rear end flange.

DETAILED DESCRIPTION OF THE EMBODIMENTS

Technical solutions in the embodiments of the present application will be described clearly and completely hereinafter in conjunction with the drawings in the embodiments of the present application. Apparently, the embodiments described in the following are only some embodiments of the present application, rather than all embodiments. Any other embodiments obtained by those skilled in the art based on the embodiments of the present application without any creative work fall within the scope of protection of the present application.

Referring to FIG. 1 to FIG. 41, an automatic syringe is provided according to the present application, which includes a housing 1, a needle guard cover 2, a push rod 3, a prompting cylinder 4, an inner tube 5, a release ring 6, a driving elastic member and a resetting elastic member. According to this solution, a pre-filled syringe 9 can be pre-assembled into the housing 1 during assembly, so that the automatic syringe delivered from the factory contains the pre-filled syringe.

The housing 1 is the main supporting and protecting component of the whole automatic syringe, and is used for fixing the syringe 9, the inner tube 5 and other components.

Figure 7:
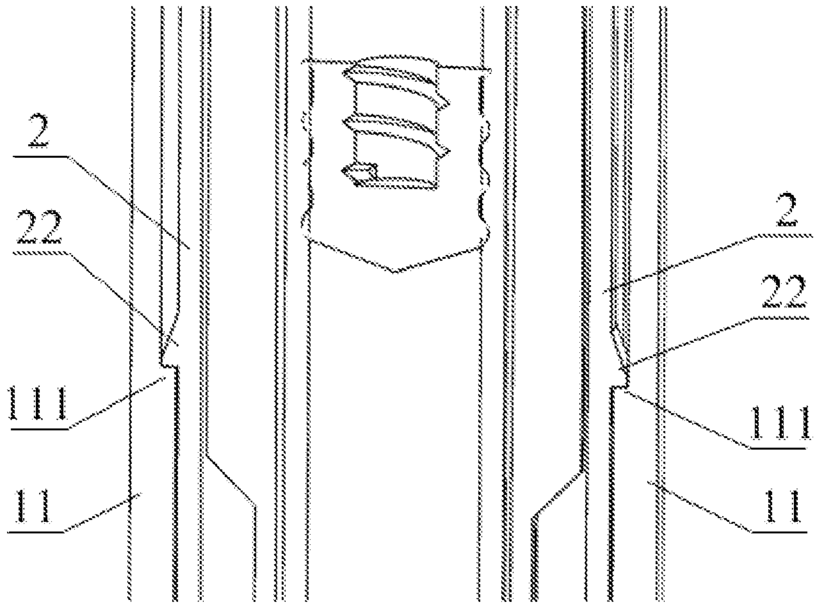
FIG. 7 is a schematic diagram showing an axial limit between a needle guard cover and the front housing in the specific embodiment of the present application.
Figure 8:
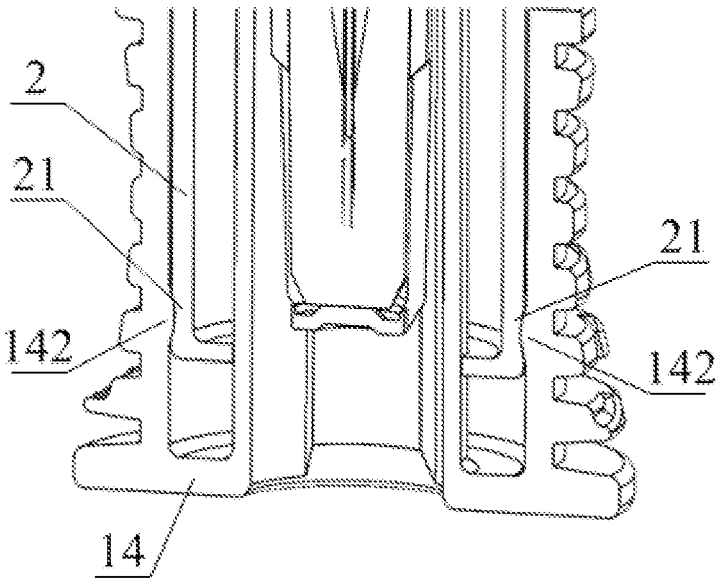
FIG. 8 is a schematic diagram showing an axial limit between the needle guard cover and the needle cap in the specific embodiment of the present application.

The housing 1 also provides a space for other components to mount and move, and may be provided as a hollow cylindrical structure as shown in FIG. 1. An ergonomic adaptation structure which is more convenient to hold by hand may be provided on the outside of the housing 1, so that the user can hold the housing 1 by hand for pressing operation during injection. A syringe fixing structure for fixing the syringe 9 is arranged in the housing 1. An opening for a needle 91 to extend out is arranged at a front end of the housing 1. The release ring 6 and the needle guard cover 2 are sequentially and slidably arranged on an inner side of the housing 1 from a rear end to the front end of the housing 1. The needle guard cover 2 can extend out of the front end of the housing 1 and slide towards the rear end relative to the housing 1 to push the release ring 6. The resetting elastic member is configured to act on the release ring 6 and drive the release ring 6 to push the needle guard cover 2 to slide towards the front end of the housing 1. The housing 1 is provided with a needle-guard-cover limiting structure for limiting a forward sliding distance of the needle guard cover 2 relative to the housing 1. Preferably, the needle-guard-cover limiting structure includes a first limiting step 111 arranged on an inner wall of the housing 1 and a second limiting step 22 arranged on an outer wall of the needle guard cover 2. As shown in FIG. 7, the needle-guard-cover limiting structure is used to prevent the needle guard cover 2 from falling out of the housing 1. The needle-guard-cover limiting structure may have other shapes and structures. For example, an inner wall of a front section of the housing 1 is provided as a tapered inner wall tapering from the rear end to the front end, and an outer wall of the needle guard cover 2 is provided as a conical outer wall that matches therewith, so as to prevent the needle guard cover 2 from falling out. Alternatively, a structure such as a limit stop pin is provided between the needle guard cover 2 and the inner wall of the housing 1, which can also play a limit role.

It should be noted that the front end mentioned in this solution refers to the end of the automatic syringe that faces towards the human body when in use for injection, that is, one end of the automatic syringe from which the needle 91 extends out; and if the automatic syringe does not contain neither the syringe 9 nor the needle 91, the front end refers to the end where the needle guard cover 2 extends out of the housing 1; the rear end mentioned in this solution is opposite to the front end mentioned above, that is, the other end of the automatic syringe opposite the front end.

The push rod 3, which is slidably arranged in the housing 1 along an axial direction, is a main component for directly pushing a piston 93 to achieve automatic injection. A front end of the push rod 3 is used to push the piston 93 in the syringe 9. The driving elastic member is configured to act on the push rod 3 and drive the push rod 3 to slide towards a front end of the syringe 9, so that the push rod 3 can automatically complete the injection action under the elastic force of the driving elastic member. The driving elastic member and the push rod 3 can be kept in the initial assembly state under the limitation of other components, so as to prevent the liquid drug in the syringe 9 from being pushed out by the push rod 3. A push-rod limiting structure is arranged on an outer circumference of the push rod 3, which is used for interacting with other components to keep the push rod 3 in the initial assembly state.

The prompting cylinder 4 is a main action component that issues a prompt signal after the injection by the push rod 3 is completed. The prompting cylinder 4 is slidably sleeved on the outer circumference of the push rod 3 along the axial direction. The driving elastic member is configured to act on the prompting cylinder 4 and drive the prompting cylinder 4 to slide towards the rear end of the housing 1, so that the prompting cylinder 4 can realize the function of signaling and prompting under the elastic force of the driving elastic member. The driving elastic member and the prompting cylinder 4 can be kept in the initial assembly state under the limitation of other components, so as to prevent the prompting cylinder 4 from sliding towards the rear end of the housing 1. The prompting cylinder 4 is provided with a push-rod-limiting cooperating structure. A prompting-cylinder limiting structure is arranged between the prompting cylinder 4 and the inner tube 5, so as to fix the position of the prompting cylinder 4 relative to the inner tube 5 in the initial assembly state.

It should be noted that the push rod 3 in the present application may be provided as a solid or hollow rod structure, or a tubular structure, etc. The driving elastic members may be a spiral spring, an elastic rope, a metal elastic sheet, etc. Preferably, the push rod 3 in this solution is of a hollow rod-shaped structure, and the driving elastic member is a push rod spring 7 arranged inside the push rod 3, where the push rod spring 7 is compressed between the front end of the push rod 3 and a rear end of the prompting cylinder 4. Since the push rod spring 7 is in a compression state, the push rod spring 7 can exert pressure directed toward the front end of the housing 1 on the push rod 3, and exert pressure directed toward the rear end of the housing 1 on the prompting cylinder 4. Once the push rod 3 is no longer subject to the axial limit of the inner tube 5, the push rod 3 moves towards the front end of the housing 1 under the elastic force of the push rod spring 7, and pushes the piston 93 for injection at the same time. Once the prompting cylinder 4 is no longer subject to the axial limit of the inner tube 5, the prompting cylinder 4 moves towards the rear end of the housing 1 under the elastic force of the push rod spring 7, and issues a prompt signal at the same time.

Preferably, a spring guide rod 71 is slidably arranged in the push rod 3. The push rod spring 7 is sleeved on an outer circumference of the spring guide rod 71. A rear end of the push rod spring 7 abuts against a guide rod end 711 at a rear end of the spring guide rod 71, and a front end of the push rod spring 7 abuts against the front end of the push rod 3. The spring guide rod 71 serves as a guide for the push rod spring 7, so that the push rod spring 7 can retract or extend along the spring guide rod 71 during the compression process or the reset release process, thereby reducing the torsion of the push rod spring 7 and ensuring the smooth extension and retraction of the push rod spring 7.

The inner tube 5 is a tubular part with a fixed position relative to the housing 1, which can provide guidance for the axial movement of the prompting cylinder 4. The inner tube 5 can work jointly with the release ring 6 in the initial assembly state to fix the push rod 3 and the prompting cylinder 4, and can release the push rod 3 after the release ring 6 moves toward the rear end, thereby achieving the automatic injection function of the push rod 3. The inner tube 5 is fixed inside the housing 1 and sleeved on an outer circumference of the prompting cylinder 4. The release ring 6 is slidably sleeved on an outer circumference of the inner tube 5. The inner tube 5 is provided with a first clip 55 capable of elastically moving along a radial direction, and the first clip 55 is deviated radially outward under its own elastic force, so that the first clip 55 can stop axially fixing the push rod 3 in time when it is no longer subject to the limiting action of the release ring 6, thereby achieving automatic injection.

Figure 12:
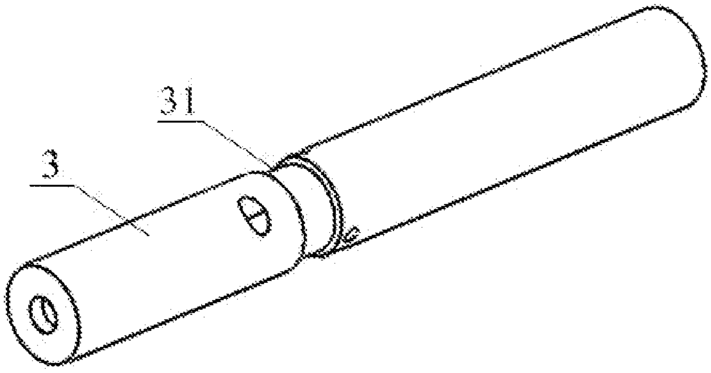
FIG. 12 is a schematic diagram of an external structure of a push rod in the specific embodiment of the present application.
Figure 13:
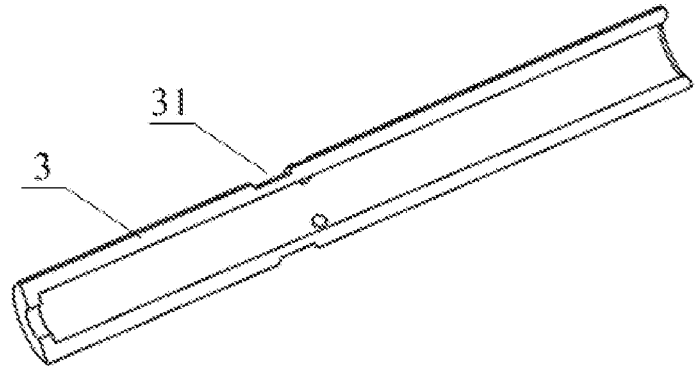
FIG. 13 is a schematic diagram of a hollow structure of the push rod in the specific embodiment of the present application.
Figure 14:
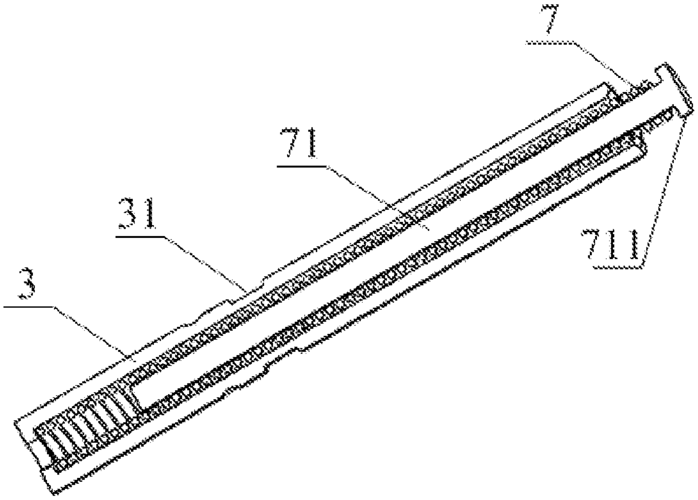
FIG. 14 is an assembly view of the push rod and a push rod spring in the specific embodiment of the present application.
Figure 15:
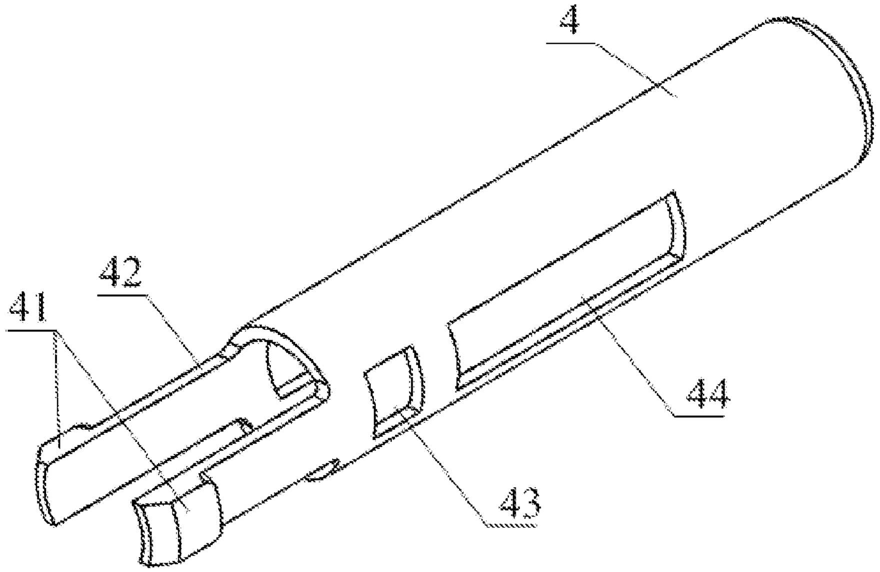
FIG. 15 is a schematic diagram of an external structure of a prompting cylinder in the specific embodiment of the present application.
Figure 16:
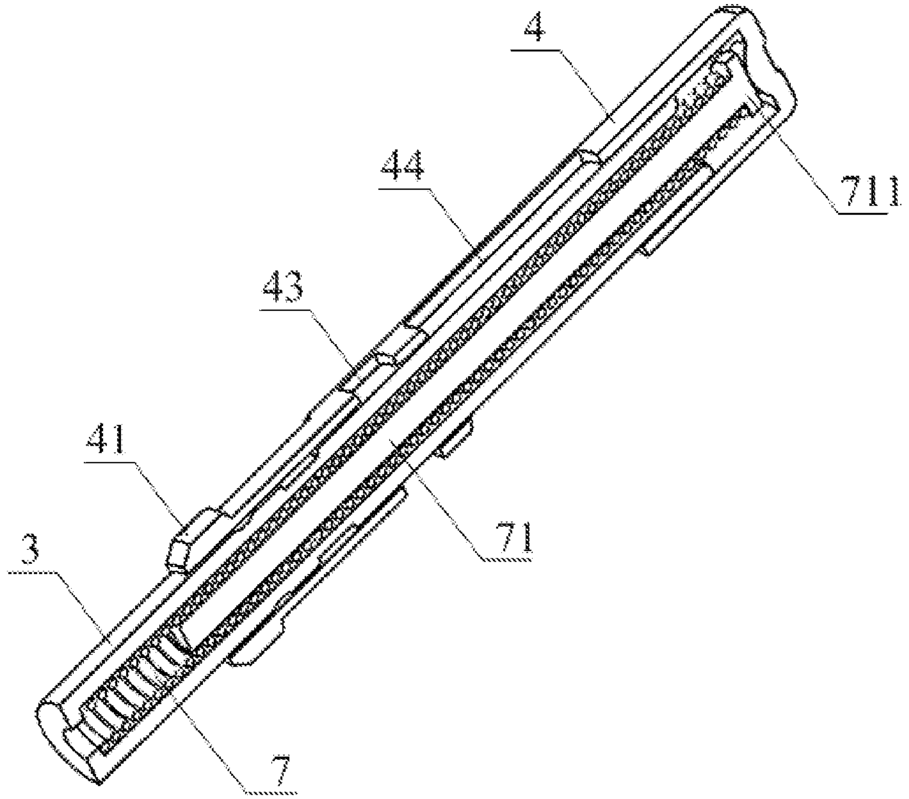
FIG. 16 is a schematic diagram of an internal structure of an assembly of the prompting cylinder and the push rod in the specific embodiment of the present application.
Figure 17:
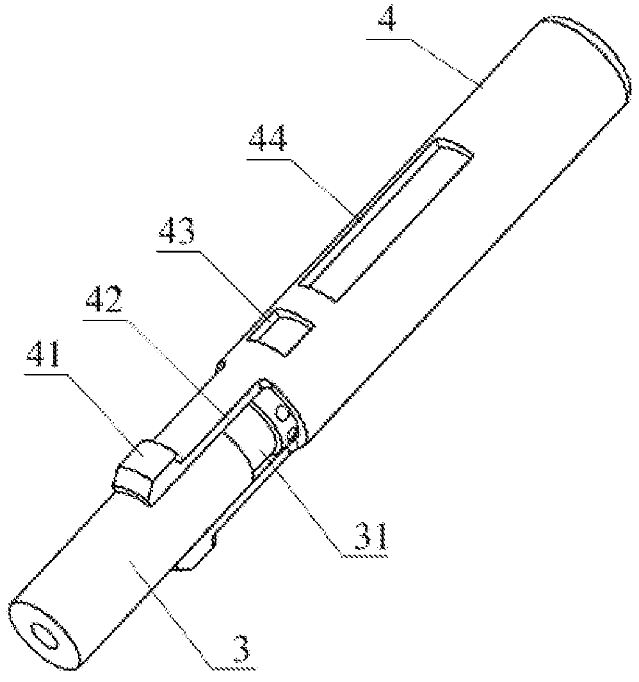
FIG. 17 is a schematic diagram of an external structure of the assembly of the prompting cylinder and the push rod in the specific embodiment of the present application.

When the automatic syringe is in the initial assembly state, that is, a state before injection, the release ring 6 can press the first clip 55 radially towards the prompting cylinder 4 and the push rod 3, that is, the first clip 55 is deviated radially inward under the limiting action of the inner wall of the release ring 6, and is snap-fitted and position-limited with the push-rod limiting structure through the push-rod-limiting cooperating structure, so as to fix the axial position of the push rod 3 by the first clip 55 and prevent the push rod 3 from moving axially before injection. The push-rod limiting structure may be provided as a pit structure, a groove structure, or a serrate structure capable of forming an axial limit with the first clip 55. Preferably, the push-rod limiting structure in this solution is provided as a push-rod ring groove 31 arranged around the circumference of the push rod 3, as shown in FIG. 12 to FIG. 14. The push-rod-limiting cooperating structure is used to provide an avoidance space for the snap-fitting between the first clip 55 and the push-rod limiting structure, or to transfer the clamping force of the first clip 55 to the push-rod limiting structure. Preferably, the push-rod-limiting cooperating structure is a prompting-cylinder avoidance notch 42 defined in a side wall of the prompting cylinder 4, and the prompting-cylinder avoidance notch 42 extends along an axial direction of the prompting cylinder 4, as shown in FIG. 15 and FIG. 17.

In addition, under the support of an outer wall of the push rod 3, the prompting-cylinder limiting structure can limit the sliding of the prompting cylinder 4 relative to the inner tube 5. After the push rod 3 has slid towards the front end for a preset distance, the prompting-cylinder limiting structure is no longer supported by the push rod 3, so that the push rod 3 stops axially fixing the prompting cylinder 4 after injecting a preset amount of liquid drug or after the injection is finished, and the driving elastic member can thereby push the prompting cylinder 4 towards the rear end of the housing 1, and a prompt signal can be issued at the same time. The prompting-cylinder limiting structure may be provided as a pin, a protrusion, a serrate structure, or the like. Preferably, the prompting-cylinder limiting structure includes a prompting-cylinder protrusion 41 arranged on an outer wall of the prompting cylinder 4, and an inner-tube clamping hole 53 defined in the inner tube 5 for clamping and limiting the prompting-cylinder protrusion 41, as shown in FIG. 15 to FIG. 19.

Figure 29:
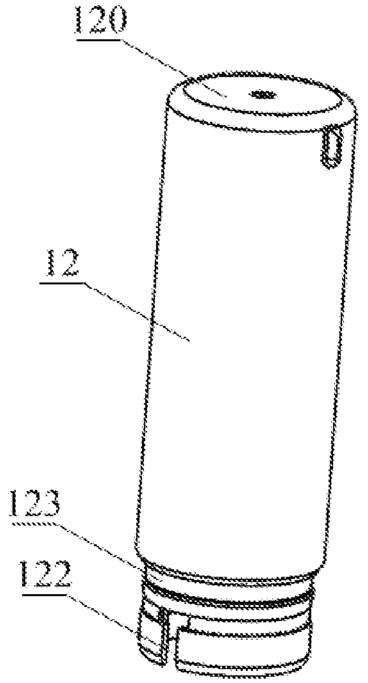
FIG. 29 is a schematic structural diagram of a rear housing in the specific embodiment of the present application.
Figure 30:
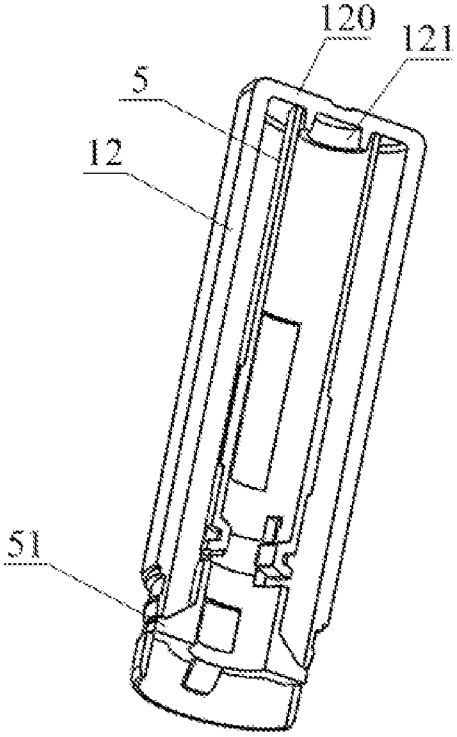
FIG. 30 is an assembly view of the rear housing and the inner tube in the specific embodiment of the present application.

It should be noted that after the injection by the push rod 3 is completed, the support for the prompting-cylinder limiting structure is removed, so that the prompting cylinder 4 can be driven by the driving elastic member to move towards the rear end of the housing 1. In the movement process of the prompting cylinder 4 or when the prompting cylinder 4 reaches a designated position, different types of prompt signals can be issued in various ways to remind the user that the injection is finished. For example, the prompting cylinder 4 can collide with a structure located in the rear of the housing 1 to send out an audible prompt signal; or send out an audible prompt signal through the mutual friction between the prompting cylinder 4 and the inner wall of the inner tube 5 during the backward movement of the prompting cylinder 4. Alternatively, a through hole is defined at a rear end of the housing 1, and the prompting cylinder 4 can slide out of the through hole, so that the prompting cylinder 4 can hit the user's hand to generate a tactile reminding signal. Alternatively, a buzzer or a reminding light is triggered when the prompting cylinder 4 slides to a certain position, so as to realize audio or light reminding. Preferably, the solution adopts a way of audio reminding to remind the user that the injection is finished, and a signal structure is arranged at the rear end of the housing 1 and used for colliding and position-limiting with the prompting cylinder 4. Specifically, the signal structure may be an end plate structure at the rear end of the housing 1, or a pressure-induced sounding structure arranged at the rear end of the housing 1, or a metal sheet, and so on. Preferably, the signal structure in this solution is an end plate 120 fixed to the rear end of the housing 1, as shown in FIG. 29 and FIG. 30. After the injection by the push rod 3 is completed, the prompting cylinder 4 impacts the end plate 120 at the rear end and makes an impact sound at the same time, thus reminding the user. In order to increase the impact sound and facilitate the user's auditory recognition, the end plate 120 in this solution is provided as a structure with large rigidity, such as glass plate, resin plate, and metal plate. Alternatively, one side of the end plate 120 facing towards the prompting cylinder 4 is provided with a metal sheet or a glass sheet with high rigidity, so that a crisp and easily recognizable sound prompt signal can be issued when the end plate and the prompting cylinder collide with each other.

Figure 4:
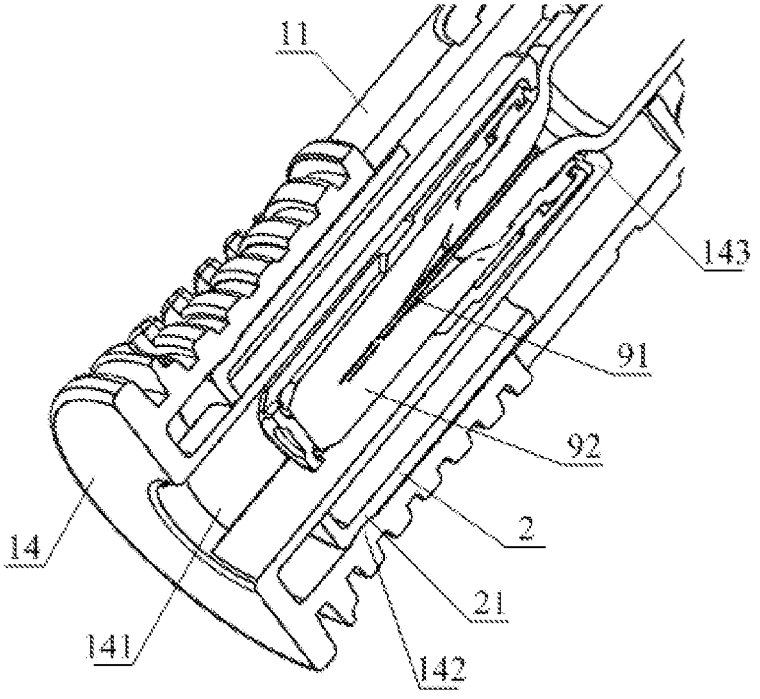
FIG. 4 is a schematic diagram of the position relationship between a needle cap, a syringe and a needle sheath in the specific embodiment of the present application.

It should be noted that in this solution, in the automatic syringe with the pre-filled syringe 9 in the initial assembly state, in order to protect the needle 91 from external pollution, the needle 91 can be protected by a needle sheath 92 that comes with the syringe 9. Other protective structures may also be provided at the front end of the automatic syringe to further protect the needle sheath 92 and the needle 91. The protective structure may also limit and protect the needle guard cover 2 to avoid accidentally triggering the automatic injection function. Preferably, as shown in FIG. 4, the automatic syringe provided by this solution further includes a needle cap 14 detachably connected to a front end of the needle guard cover 2. Before injection is required, the user can manually pull off the needle cap 14, so that the needle guard cover 2 can move toward the rear end of the housing 1 under the pressing action, and the needle 91 or the needle sheath 92 is thereby exposed.

Figure 5:
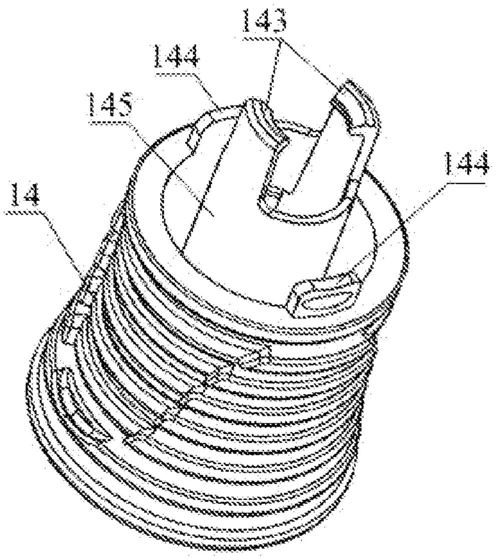
FIG. 5 is a schematic structural diagram of the needle cap in the specific embodiment of the present application.

Preferably, a rear end of the needle cap 14 is provided with a claw 143 for catching a rear end of the needle sheath 92, and the claw 143 can exert a pulling force on the needle sheath 92 towards the front end. As shown in FIG. 4 and FIG. 5, the needle cap 14 is in a tubular structure as a whole, and a needle-cap inner cylinder 145 penetrating through the needle cap 14 is provided on an inner side of the needle cap 14. A needle-sheath mounting hole 141 for accommodating the needle sheath 92 is formed in an inner ring of the needle-cap inner cylinder 145. A front end of the needle-cap inner cylinder 145 is fixedly connected with a front end of a needle cap outer cylinder, or the two may be provided as an integrated structure. A pair or multiple pairs of claws 143 are arranged at a rear end of the needle-cap inner cylinder 145. Each claw 143 is an elastic hook structure extending from a side wall of the needle-cap inner cylinder 145 towards an inner side of the needle-sheath mounting hole 141. As shown in FIG. 4 and FIG. 5, a rear end face of the claw 143 is provided as a guide slope which gradually approaches the center of the needle-cap inner cylinder 145 from the rear to the front, so that the claw 143 can be easily fitted into the rear end of the needle sheath 92. When assembling the automatic syringe, the claw 143 can be fitted into the rear end face of the needle sheath 92 from the front end to the rear end. When using the automatic syringe, the needle cap 14 is pulled off, and the needle sheath 92 is thereby detached from the needle 91 due to a pulling force exerted by the claw 143 on the needle sheath 92. The claw 143 extends inward and towards a front end of the needle cap 14, so that it can catch the needle sheath 92 more firmly and ensure the effective removal of the needle sheath 92. In addition, a space for the insertion of the front end of the needle guard cover 2 is reserved between the outer cylinder of the needle cap 14 and the needle-cap inner cylinder 145.

Preferably, an anti-dropping recess-protrusion engaging structure is arranged between an inner ring of the needle cap 14 and a circumference of the needle guard cover 2. Before using the syringe, the anti-dropping recess-protrusion engaging structure can prevent the needle cap 14 from accidentally detaching from the housing 1 or the needle guard cover 2. Specifically, as shown in FIG. 4, in this solution, the anti-dropping recess-protrusion engaging structure is arranged between the inner wall of the outer cylinder of the needle cap 14 and the outer wall of the needle guard cover 2. The anti-dropping recess-protrusion engaging structure specifically includes a needle-cap anti-dropping limiting part 142 and a needle-guard-cover anti-dropping limiting part 21. The needle-cap anti-dropping limiting part 142 shown in FIG. 4 is a protrusion, and the needle-guard-cover anti-dropping limiting part 21 is a recess engaged with the needle-cap anti-dropping limiting part 142, or vice versa. That is, the needle-cap anti-dropping limiting part 142 is a recess, and the needle-guard-cover anti-dropping limiting part 21 is a protrusion, which can also play the role of anti-dropping and limiting. In the present application, the anti-dropping recess-protrusion engaging structure may also be arranged between the needle-cap inner cylinder 145 and the needle guard cover 2, which is not described in detail here.

Figure 6:
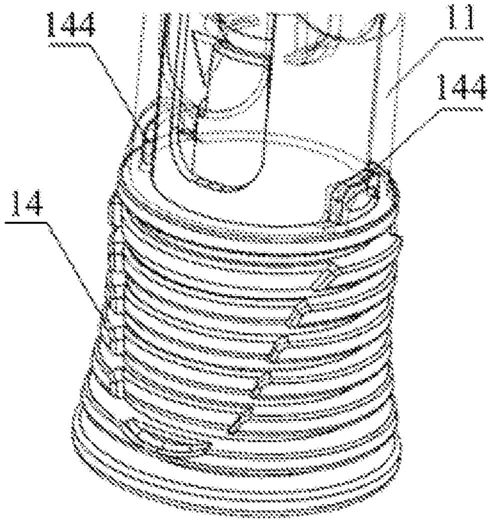
FIG. 6 is a schematic diagram of the limiting assembly of the needle cap and a front housing in the specific embodiment of the present application.

Preferably, a needle-cap limiting structure 144 is arranged between the housing 1 and the needle cap 14, which is used to limit the movement of the needle cap 14 towards the rear end relative to the housing 1. As shown in FIG. 5 and FIG. 6, the needle-cap limiting structure 144 is specifically provided as a protrusion fixed at a rear end of the outer cylinder of the needle cap 14, and the front end of the housing 1 is provided with a groove engaged with needle-cap limiting structure. When the needle cap 14 is mounted at the front end of the housing 1, the needle-cap limiting structure 144 is engaged with the groove, which cannot only restrict the needle cap 14 from moving towards the rear end relative to the housing 1, but also restrict the needle cap 14 from rotating circumferentially relative to the housing 1.

Figure 9:
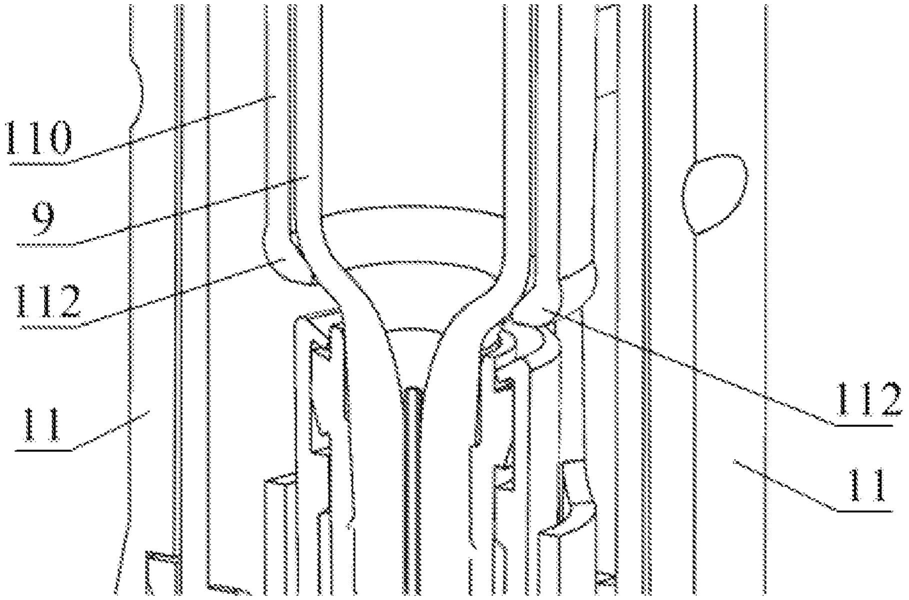
FIG. 9 is a schematic diagram showing the positioning of the front housing to the shoulder of the syringe in the specific embodiment of the present application.

As shown in FIG. 9, preferably, the syringe fixing structure is a syringe fixing cylinder 110 fixed on an inner side of the housing 1, and a front end of the syringe fixing cylinder 110 is provided with a syringe clamping claw 112 for position-limiting and cooperating with a front shoulder of the syringe 9. A main body of the syringe 9 is accommodated in the syringe fixing cylinder 110, and the front shoulder of the syringe 9 abuts against the syringe clamping claw 112. Therefore, during injection, the syringe 9 can be stably fixed in the syringe fixing cylinder 110 without shaking, and a rear end flange 94 of the syringe 9 can also be prevented from being broken, and the syringe 9 can be thereby prevented from being pressed out of the housing 1. The syringe fixing structure in the present application may also be provided as a syringe fixing ring or a syringe fixing step fixed inside the housing 1, which is not described in detail here.

Figure 10:
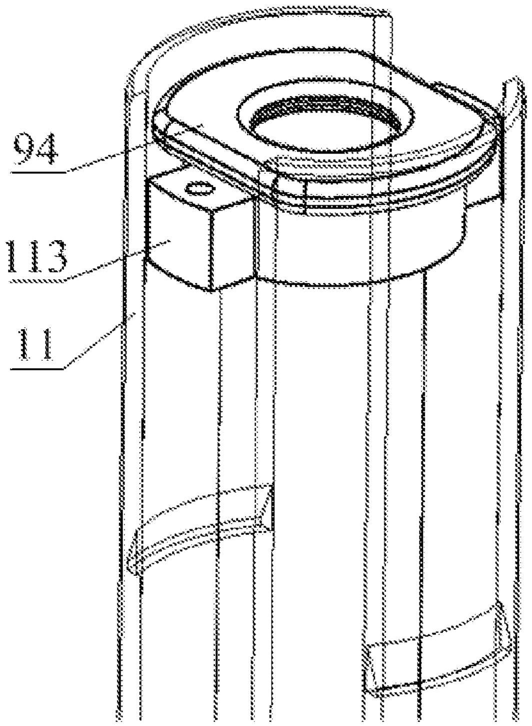
FIG. 10 is a schematic diagram of the positional relationship between a cushion block and a rear end flange in the specific embodiment of the present application.
Figure 11:
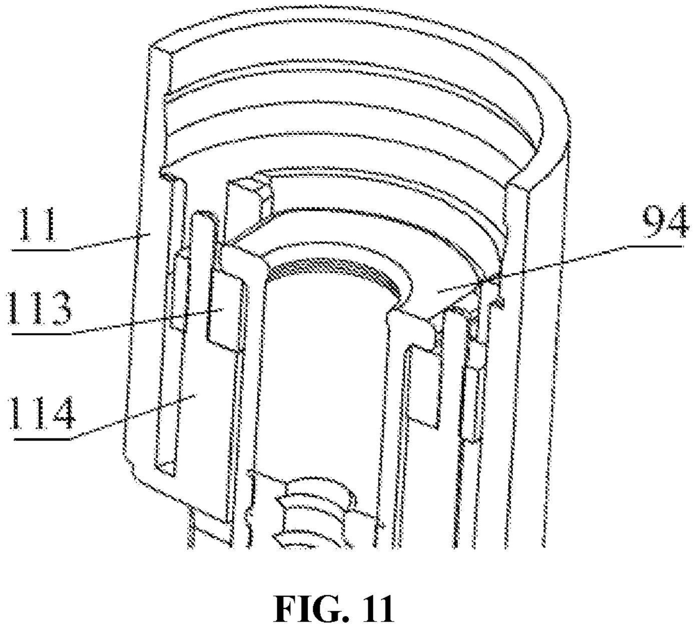
FIG. 11 is a schematic diagram of the positional relationship between the cushion block and the front housing in the specific embodiment of the present application.

As shown in FIG. 10 and FIG. 11, preferably, a rear end of the syringe fixing cylinder 110 is provided with a support body 114 for position-limiting and cooperating with the rear end flange 94 of the syringe 9, and an elastic cushion block 113 is arranged between the support body 114 and a front end face of the rear end flange 94 of the syringe 9. The main function of the elastic cushion block is to provide an elastic support for the syringe 9 during the injection process, so as to avoid the glass syringe 9 from being broken due to the excessive thrust released in an instant.

Figure 18:
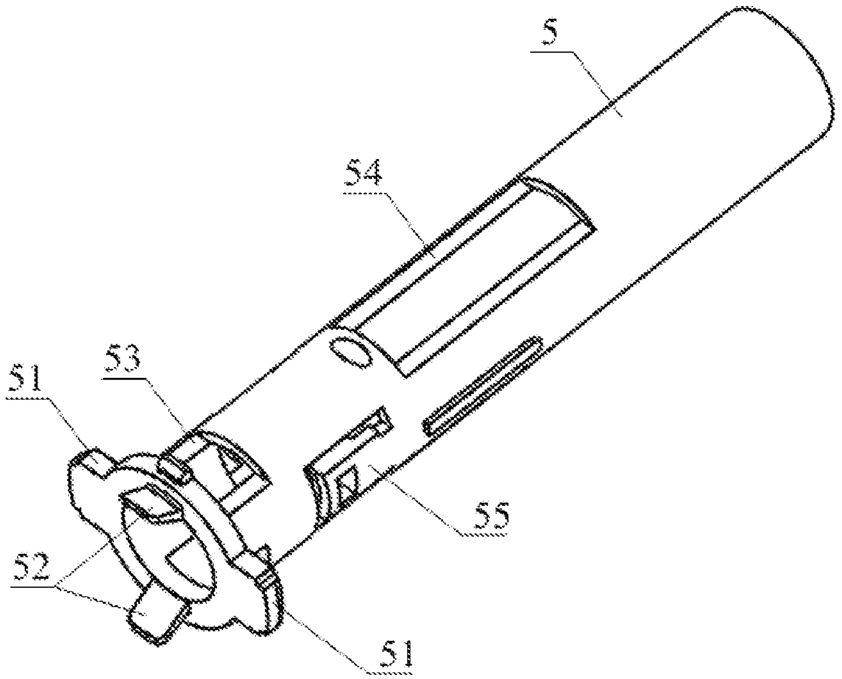
FIG. 18 is a schematic diagram of an external structure of an inner tube in the specific embodiment of the present application.
Figure 19:
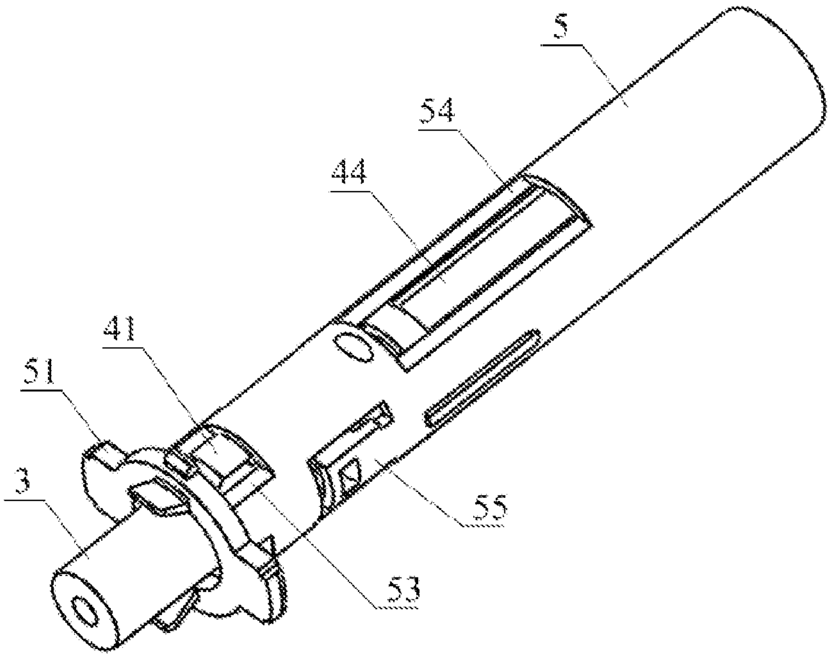
FIG. 19 is an assembly view of the inner tube, the prompting cylinder and the push rod in the specific embodiment of the present application.
Figure 20:
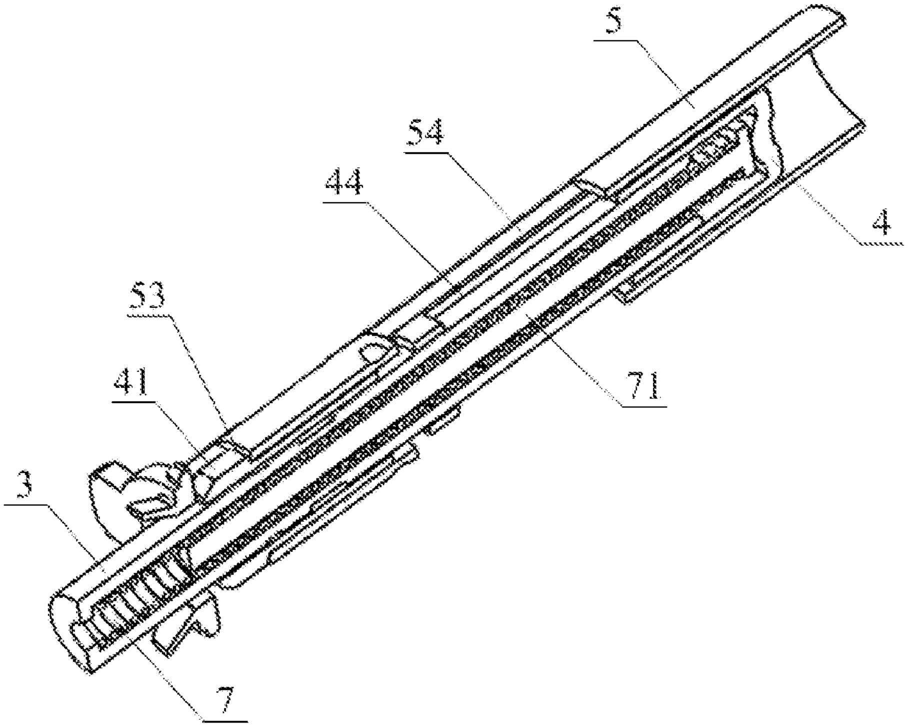
FIG. 20 is a schematic diagram of an internal structure of the assembly of the inner tube, the prompting cylinder and the push rod in the specific embodiment of the present application.
Figure 21:
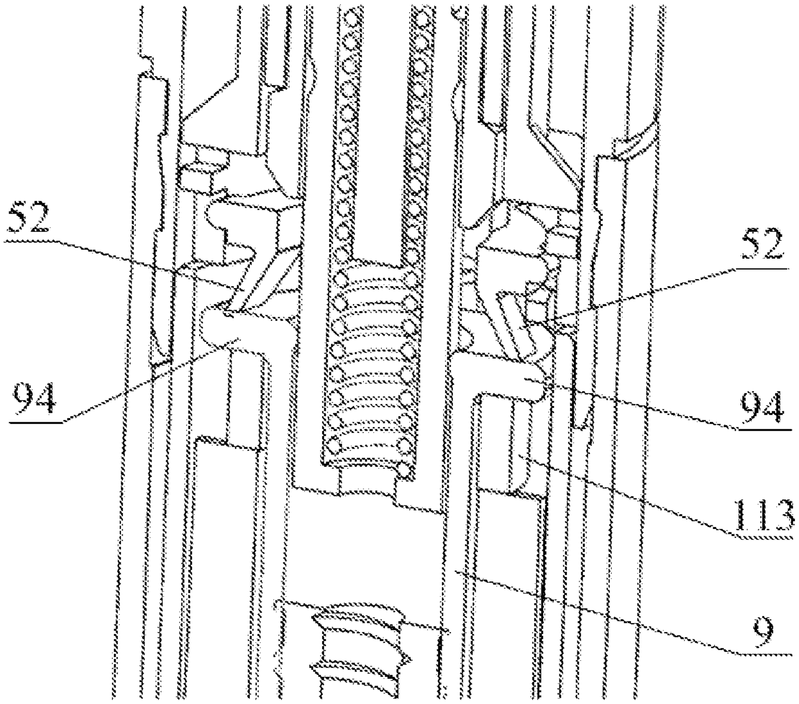
FIG. 21 is a schematic diagram of the positional relationship between the inner tube and the rear end flange in the specific embodiment of the present application.
Figure 22:
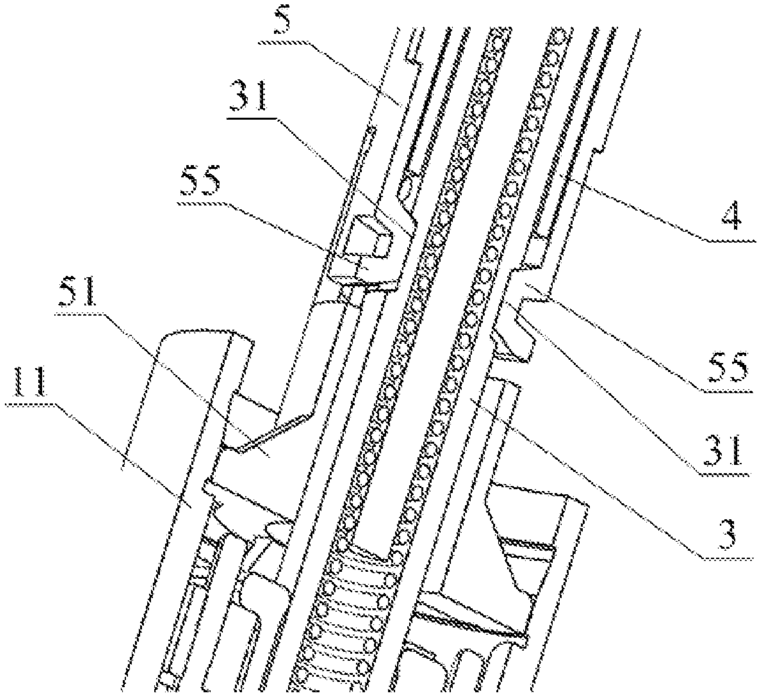
FIG. 22 is a schematic diagram showing an axial limit between the inner tube and the push rod in the specific embodiment of the present application.
Figure 23:
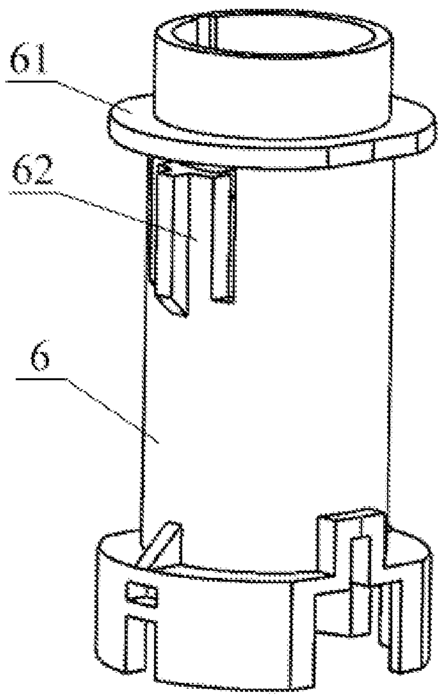
FIG. 23 is a schematic diagram of an external structure of a release ring in the specific embodiment of the present application.
Figure 24:
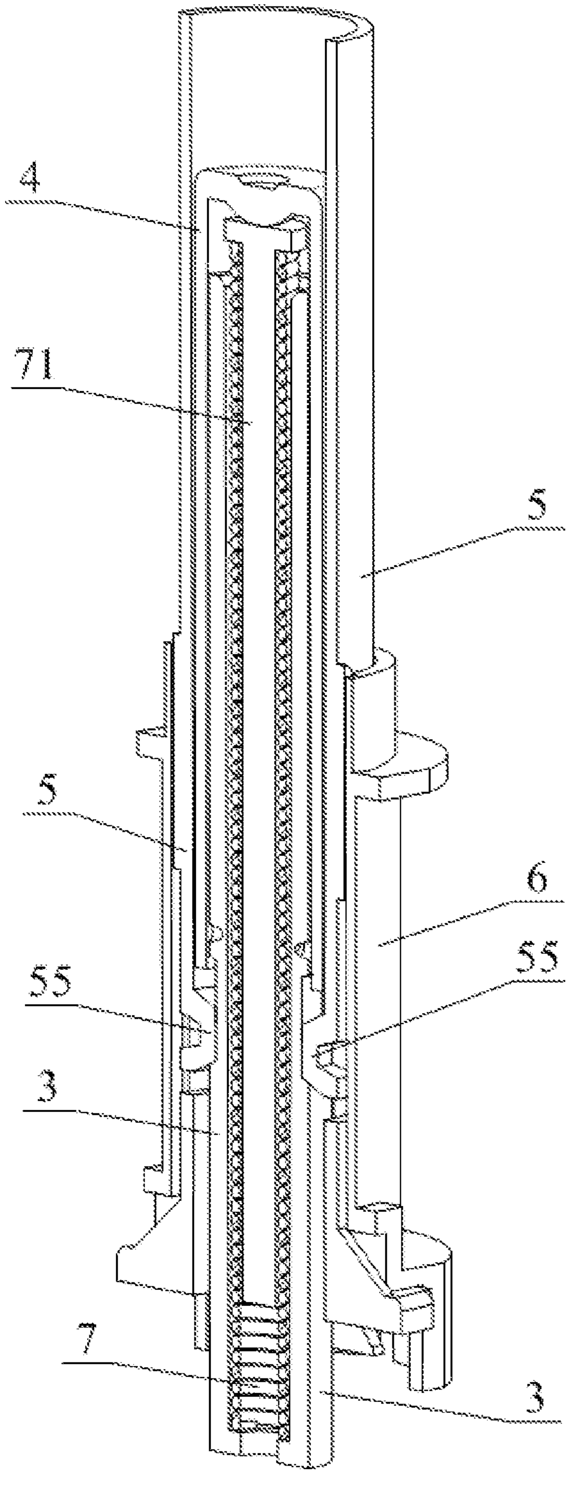
FIG. 24 is a schematic diagram of an internal structure of an assembly of the release ring, the inner tube, and the push rod in the specific embodiment of the present application.
Figure 25:
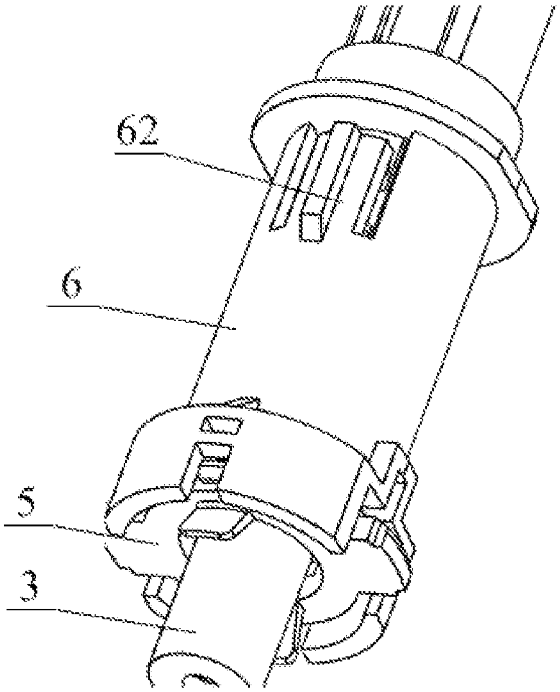
FIG. 25 is a schematic diagram of an external structure of the assembly of the release ring, the inner tube, and the push rod in the specific embodiment of the present application.

Preferably, a front end of the inner tube 5 abuts against a rear end face of the rear end flange 94 of the syringe 9, and a rear end of the inner tube 5 abuts against the rear end of the housing 1. In this way, the inner tube 5 is fixed in the housing 1 through the abutting action of two ends of the inner tube, and provides stable support for the syringe 9. Further preferably, as shown in FIG. 18 and FIG. 21, the inner-tube front end 52 abuts against the rear end flange 94 of the syringe 9, and the inner-tube front end 52 can be provided as an elastic supporting foot structure. The inner-tube front end 52 continuously presses on the rear end flange 94 to provide stable pressure, so that the rear end flange 94 of the syringe 9 is always pressed against the elastic cushion block 113, and damage to the rear end flange 94 is prevented.

Preferably, the rear end of the housing 1 is provided with an annular protrusion 121 coaxially cooperating with the rear end of the inner tube 5, and a rotation limiting structure for preventing the inner tube 5 from rotating is arranged between a side wall of the housing 1 and the inner tube 5. Specifically, the annular protrusion 121 is used to ensure that the inner tube 5 does not shake in the housing 1, so as to provide stable sliding support for the release ring 6, the prompting cylinder 4 and other components. The annular protrusion may also be used for ensuring the coaxiality of the inner tube 5 and the housing 1. When the prompting cylinder 4 moves to the rear end of the housing 1, the rear end of the prompting cylinder 4 hits a front end face of the annular protrusion 121, thereby issuing an impact sound signal to realize the prompt. The rotation limiting structure ensures that the inner tube 5 cannot rotate relative to the housing 1. The rotation limiting structure may be provided in various structural forms. For example, a limiting block structure or a limiting groove structure is arranged between the side wall of the housing 1 and the inner tube 5; or, the outer contour of the end section of the inner tube 5 is provided into a non-circular structure such as a square or an ellipse. The rotation of the inner tube 5 is limited by the cooperation of the profiles. Preferably, an inner-tube anti-rotation limiting groove 122 is defined at the inner wall of the housing 1, which can be specifically provided as a T-shaped notch groove. The front end of the inner tube 5 is provided with an inner-tube anti-rotation protrusion 51 corresponding to the inner-tube anti-rotation limiting groove 122, as shown in FIG. 29 and FIG. 30.

It should be noted that, the housing 1 of the automatic syringe provided by the present application can be provided as an integral structure or a split structure, such as a cylindrical structure divided into two or more sections. Preferably, as shown in FIG. 1, the housing 1 includes a front housing 11 and a rear housing 12, and the front housing 11 is connected to a front end of the rear housing 12. The front housing 11 mainly provides mounting support for the pre-filled syringe 9 and ensures that the needle guard cover 2 maintains stable axial movement. The rear housing 12 mainly provides mounting space for other components such as the inner tube 5 and the resetting elastic member. Specifically, the front housing 11 and the rear housing 12 can be connected and fixed in various ways, such as threaded connection, snap connection, etc. Preferably, in this solution, a rear-housing mounting ring groove 123 is provided at the front end of the rear housing 12 for connecting with the front housing 11 for fixation, as shown in FIG. 29. Further preferably, when the automatic syringe according to this solution is delivered as a semi-finished product, the housing 1 is of a split design. The syringe assembly plant assembles the pre-filled syringe 9 into the housing 1, and then connects the front housing 11 with the rear housing 12 for fixation. In order to prevent the user from reusing the syringe, an anti-disassembly structure is further provided at the joint of the front housing 11 and the rear housing 12. For example, the front housing and the rear housing are fixed by gluing or by interference fit, or the joint of the two housings is provided as a fragile disposable connection structure which cannot be connected again after disassembly.

Preferably, in order to make it easier for the user to observe the injection by the push rod 3, the housing 1 and the needle guard cover 2 are each provided with an observation window 13 extending in the axial direction. The observation window is a hollow opening defined in the side walls of the housing 1 and the needle guard cover 2. In the present application, the observation window 13 may also be provided as a transparent cover structure; or the housing 1, the needle guard cover 2 and other components located at the circumference of the syringe 9 and the syringe 9 itself are provided as transparent structures, which is also easy for the user to observe the injection situation.

The release ring 6 is a sliding member with a cylindrical structure. The main function of the release ring is to restrain the first clip 55 of the inner tube 5 from bouncing outward in the initial assembly state, so as to ensure that the push rod 3 is fixed before injection. When the release ring 6 moves towards the rear end of the housing 1 and stops radially fixing the first clip 55, the first clip 55 stops axially limiting the push rod 3, so that the push rod 3 can achieve automatic injection under the action of the push rod spring 7. Another function of the release ring 6 is to be able to interact with the prompting cylinder 4 after the injection is completed and the release ring 6 returns to the initial axial position, thus ensuring that the syringe cannot be reused.

Figure 26:
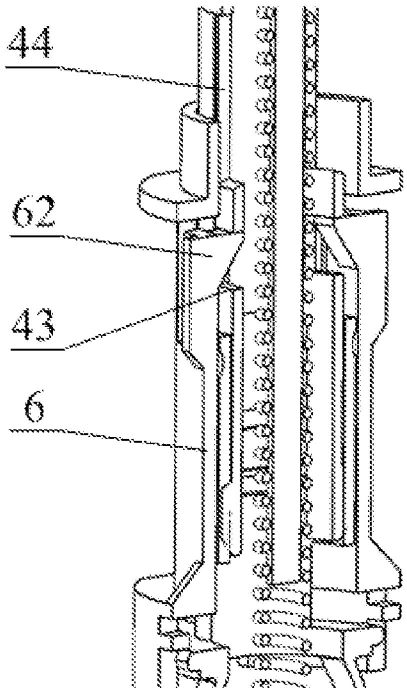
FIG. 26 is a schematic diagram showing an axial limit between the release ring and the prompting cylinder in the specific embodiment of the present application.
Figure 27:
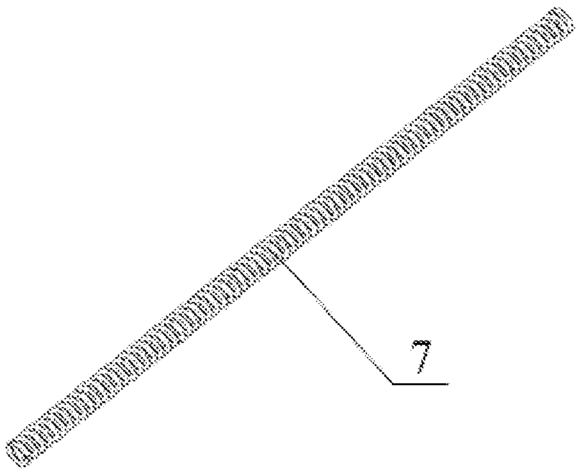
FIG. 27 is a schematic structural diagram of a push rod spring in the specific embodiment of the present application.
Figure 28:
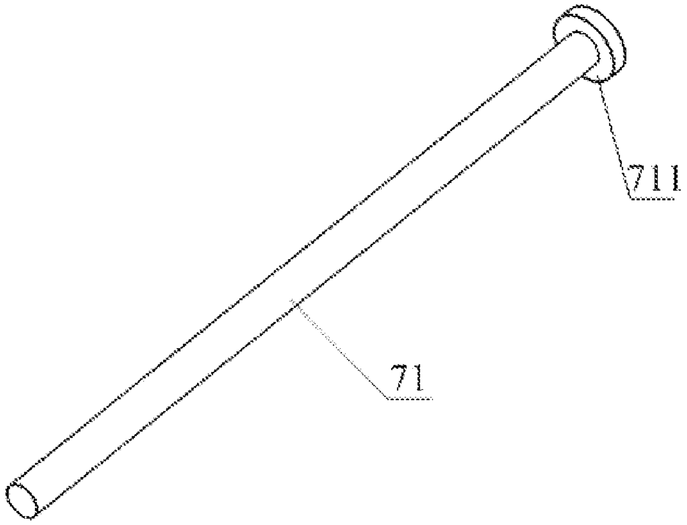
FIG. 28 is a schematic structural diagram of a spring guide rod in the specific embodiment of the present application.

When injection is needed, the needle guard cover 2 drives the release ring 6 to overcome the elastic force of the resetting elastic member together, thus driving the release ring 6 to move towards the rear end of the housing 1. In order to facilitate the sliding of the release ring 6 relative to the inner tube 5, preferably, the inner tube 5 is provided with an inner-tube avoidance slot hole 54 extending along the axial direction, where the release ring 6 is provided with a second clip 62 which is in sliding fit with the inner-tube avoidance slot hole 54 and can interact with the prompting cylinder 4, and an outer side of the prompting cylinder 4 is provided with a clip limiting structure used for limiting the movement of the second clip 62 towards the rear end of the housing 1. The second clip 62 may be provided as an elastic clip structure capable of elastic deformation in the radial direction. The second clip 62 can interact with the prompting cylinder 4 so that the second clip and the prompting cylinder abut against each other or rub against each other in the axial direction. When the injection is finished, the prompting cylinder 4 moves to the rear end of the housing 1, and the front end of the needle guard cover 2 moves away from the injection site. At this time, the release ring 6 moves towards the front end under the action of the resetting elastic member. When the second clip 62 of the release ring 6 moves to the position where it interacts with the clip limiting structure of the prompting cylinder 4, the release ring 6 cannot move towards the rear end of the housing 1 again due to the axial limiting effect of the clip limiting structure on the second clip 62, so that the automatic syringe cannot be used twice for injection, and the use safety is ensured. The clip limiting structure may be provided into various structural forms, such as limiting hole structure, limiting serrate structure, and limiting friction surface structure. Preferably, in this solution, the side wall of the prompting cylinder 4 is provided with a clip limiting opening 43, as shown in FIG. 15 to FIG. 17 and FIG. 26. As can be seen from the figures, in the initial assembly state, the clip limiting opening 43 is located at the front end of the second clip 62, so that the clip limiting opening 43 cannot limit the second clip 62 in the axial direction. When the injection is completed (as shown in FIG. 26), the second clip 62 moves towards the front end and is fitted into the clip limiting opening 43. At this time, an inner edge of a rear end of the clip limiting opening 43 abuts against a rear end face of the second clip 62, thereby restraining the second clip 62 from again moving towards the rear end of the housing 1. In addition, in order to facilitate the relative movement between the second clip 62 and the prompting cylinder 4, in this solution, a clip avoidance opening 44 is further defined in the side wall of the prompting cylinder 4, as shown in FIG. 15 to FIG. 17 and FIG. 26. The clip avoidance opening 44 is located at the rear end of the clip limiting opening 43.

Figure 31:
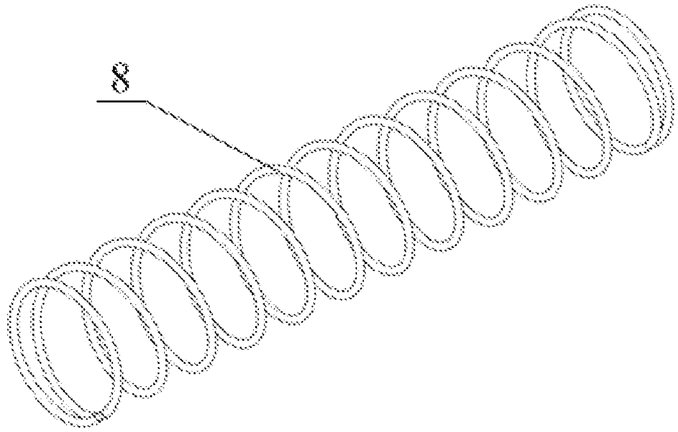
FIG. 31 is a schematic structural diagram of a reset spring in the specific embodiment of the present application.
Figure 34:
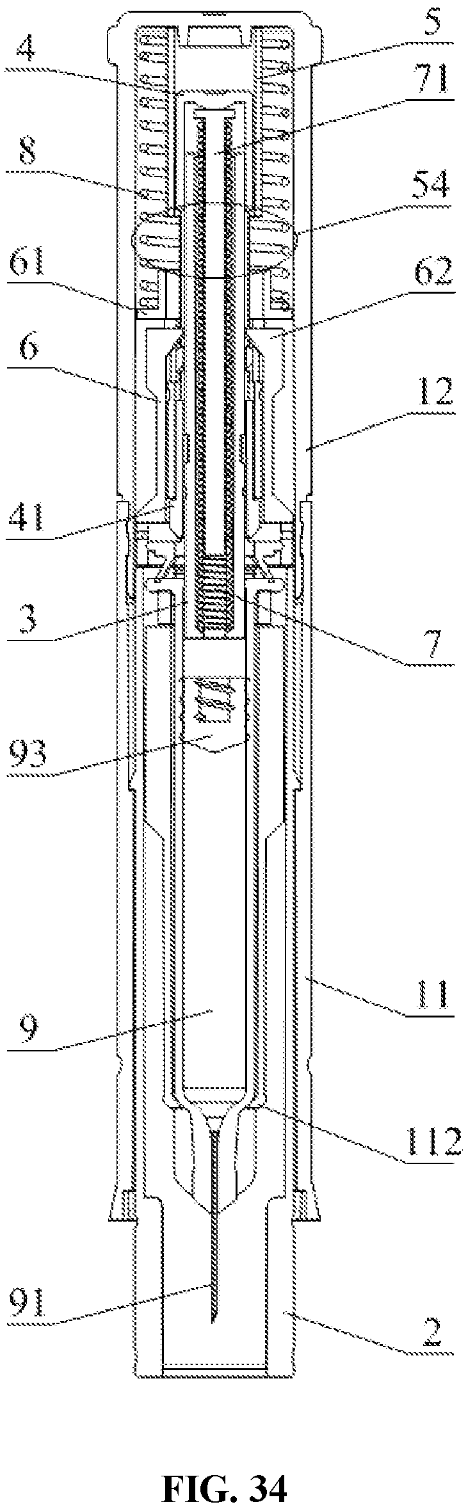
FIG. 34 is a first longitudinal sectional diagram of the automatic syringe during use in the specific embodiment of the present application.

It should be noted that, the resetting elastic member serves as a holding member to keep the release ring 6 and the needle guard cover 2 in the initial axial position, and serves as a restoring member to restore the release ring 6 and the needle guard cover 2 to the initial axial position after injection. The resetting elastic member can provide the release ring 6 with a continuous elastic force directed toward the front end. The resetting elastic member may specifically adopt elastic members such as spiral springs, elastic ropes or metal spring sheets. Preferably, the resetting elastic member is a reset spring 8, as shown in FIG. 31. The reset spring 8 is compressed between the release ring 6 and the housing 1. As shown in FIG. 34, in this solution, a release-ring rear end flange 61 is further provided at the rear end of the release ring 6 for abutting against the reset spring 8. A front end of the reset spring 8 abuts against the release-ring rear end flange 61, and a rear end of the reset spring 8 abuts against an inner wall of a rear end of the rear housing 12. The reset spring 8 may also be in a compressed state in the initial assembly state.

The needle cap 14, the needle guard cover 2, the front housing 11 and the elastic cushion block 113 described above constitute a holding assembly of the front housing, which is mainly used for holding and fixing the position of the syringe 9. The push rod 3, the prompting cylinder 4, the inner tube 5, the release ring 6, the push rod spring 7, the spring guide rod 71, the reset spring 8, and the rear housing 12 described above constitute a driving assembly of the rear housing, which is mainly used to drive the injection.

It should be noted that, each component of the automatic syringe of the present application may be made of various materials (such as resin and metal commonly used in medical equipment), and may also have different specifications and structures.

Next, with reference to FIG. 1 to FIG. 3 and FIG. 32 to FIG. 41, the complete use process of the automatic syringe provided by the present application is described as follows.

Figure 2:
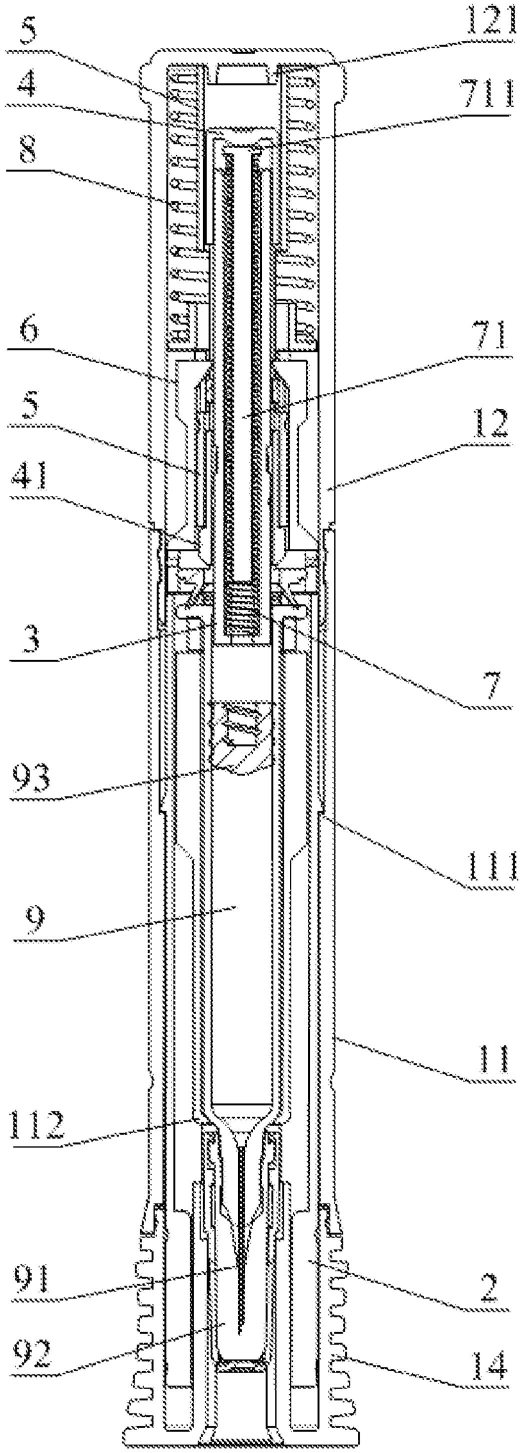
FIG. 2 is a schematic diagram of an internal structure of the automatic syringe along a first section in the specific embodiment of the present application.
Figure 3:
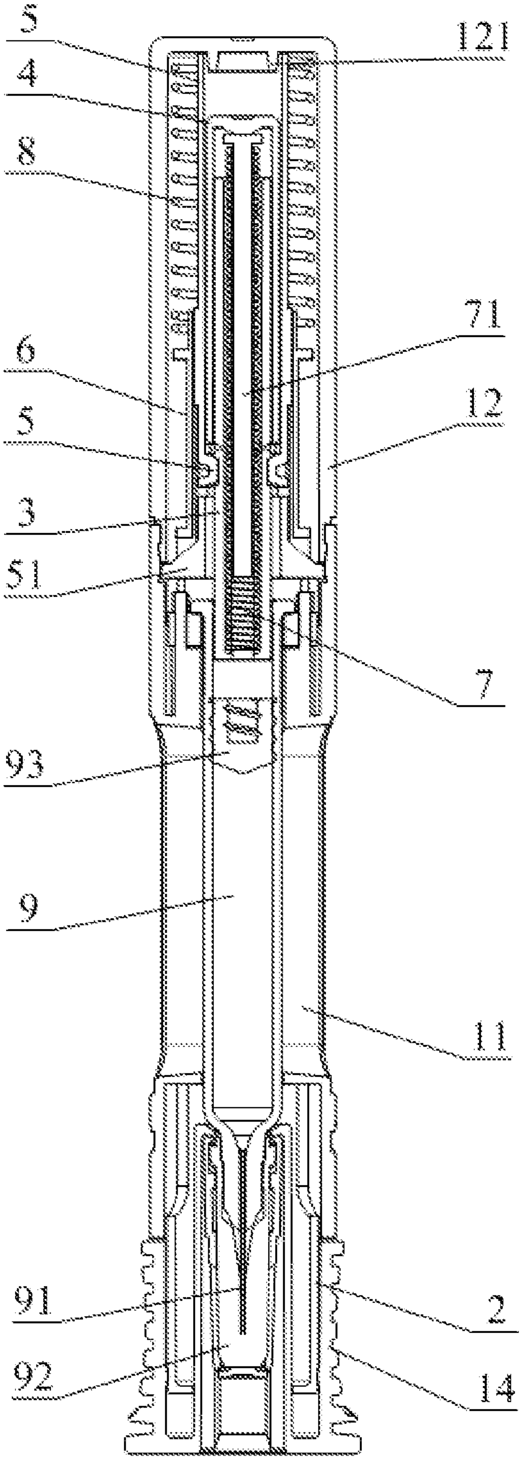
FIG. 3 is a schematic diagram of the internal structure of the automatic syringe along a second section in the specific embodiment of the present application.

FIG. 1 to FIG. 3 are schematic views of the overall external structure and two longitudinal cross-sections of the automatic syringe before use, where the needle cap 14 of the automatic syringe is mounted at the front end of the housing 1. The front housing 11 is adapted to hold the syringe 9 containing the drug. The syringe 9 may be a pre-filled syringe and has the needle 91 arranged at the front end of the syringe 9. In other embodiments, the syringe 9 may be a drug cartridge suitable for detachably connecting with the needle 91. The needle 91 is directed towards a front opening of the front housing 11 and is protected by the needle sheath 92. In an initial assembly state before injection, the needle guard cover 2 is extended out of the front end of the housing 1 to protect the needle 91 and the needle sheath 92.

Figure 32:
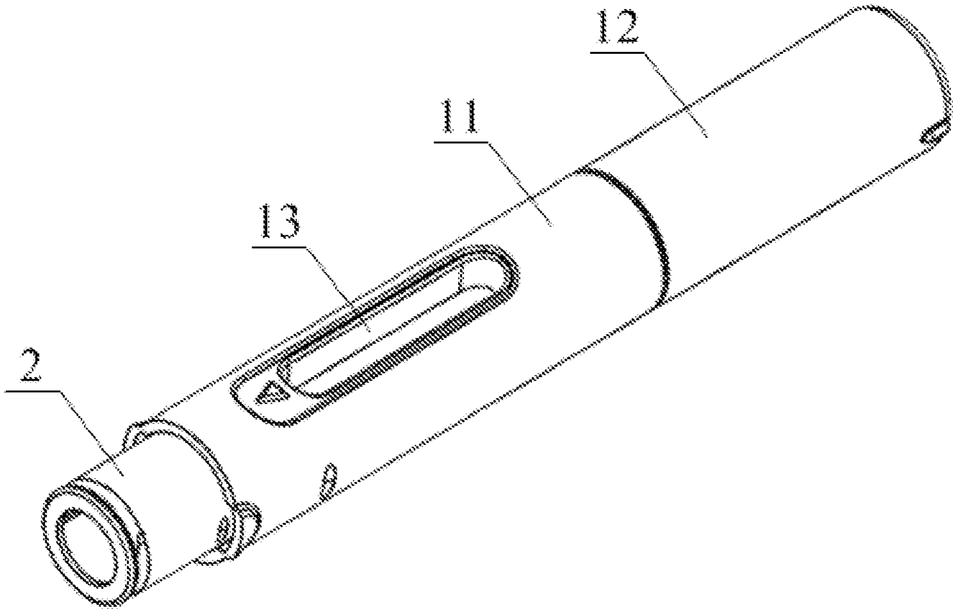
FIG. 32 is a schematic structural diagram of the automatic syringe with the needle cap being removed in the specific embodiment of the present application.
Figure 33:
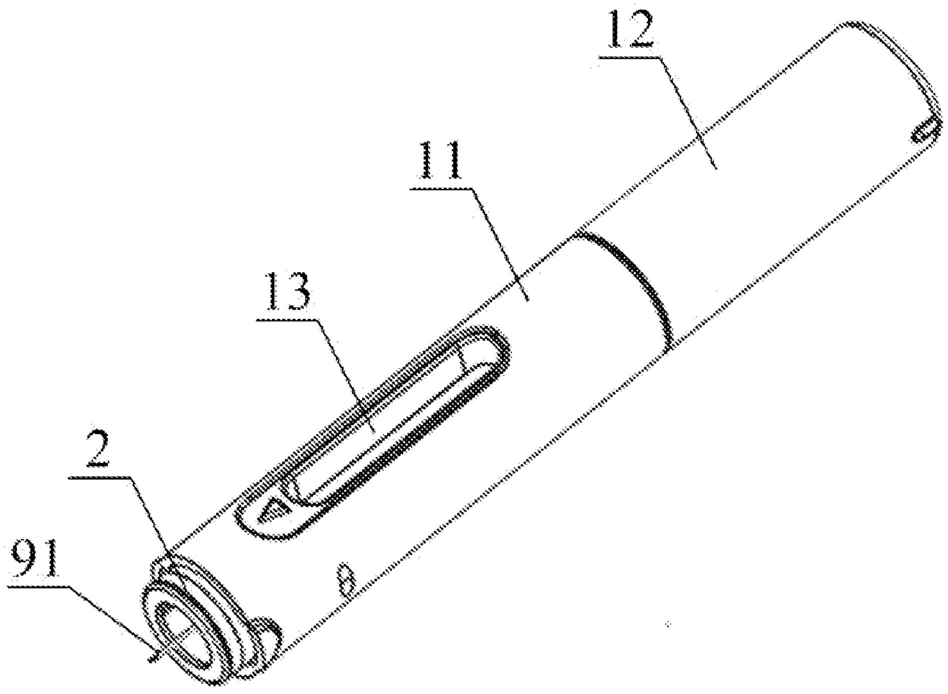
FIG. 33 is a schematic structural diagram of the automatic syringe in the specific embodiment of the present application, where the needle is exposed after the needle guard cover is retracted.
Figure 35:
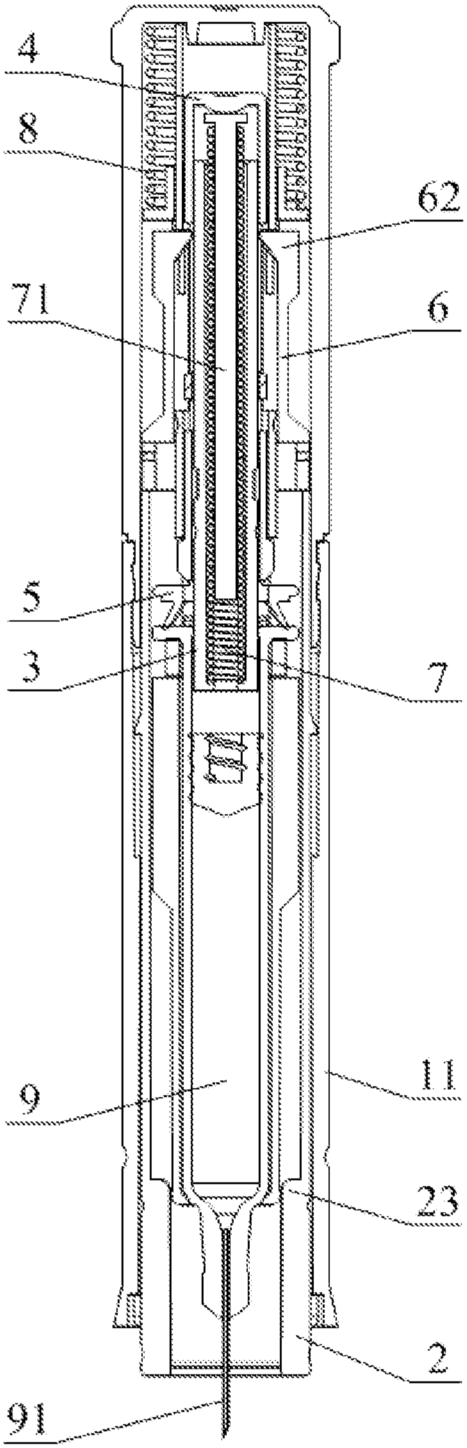
FIG. 35 is a second longitudinal sectional diagram of the automatic syringe during use in the specific embodiment of the present application.

As shown in FIG. 32, when preparing for injection, the needle cap 14 is pulled off from the front end, the front end of the needle guard cover 2 is exposed outside the housing 11, and the needle 91 is still covered by the needle guard cover 2. Then the housing 1 is held by hand with the front end of the housing 1 being aligned with the part of the body to be injected, and the needle guard cover 2 is aligned with the part to be injected and is pressed firmly. At this time, the needle guard cover 2 retracts to the inside of the housing 1 to expose the needle 91, so that the needle 91 can pierce into the part to be injected. When the needle guard cover 2 is pushed backward, the rear end face of the needle guard cover 2 abuts against the front end of the release ring 6, the needle guard cover 2 overcomes the elastic force of the reset spring 8 and drives the release ring 6 to move together towards the rear end relative to the housing 1 to compress the reset spring 8, until the second clip 62 of the release ring 6 abuts against the inner-tube avoidance slot hole 54 of the inner tube 5, as shown in FIG. 33 to FIG. 35.

Meanwhile, the needle-guard-cover inner ring protrusion 23 arranged on the inner wall of the needle guard cover 2 abuts against the syringe clamping claw 112 inside the front housing 11 to provide auxiliary support for the front shoulder of the syringe 9.

Figure 36:
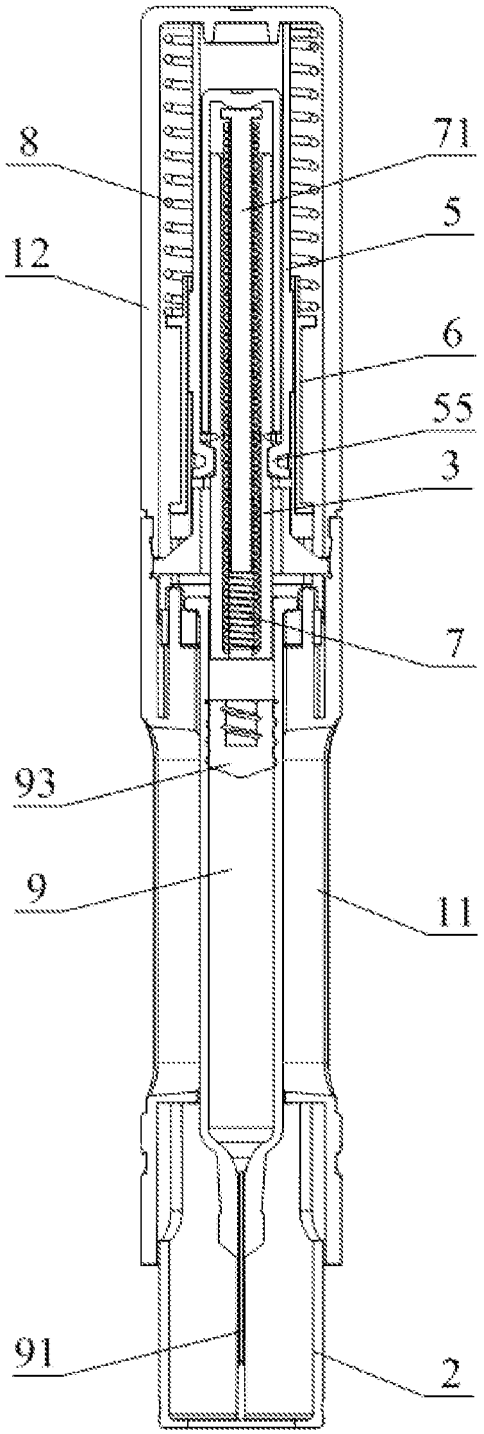
FIG. 36 is a third longitudinal sectional diagram of the automatic syringe during use in the specific embodiment of the present application.
Figure 37:
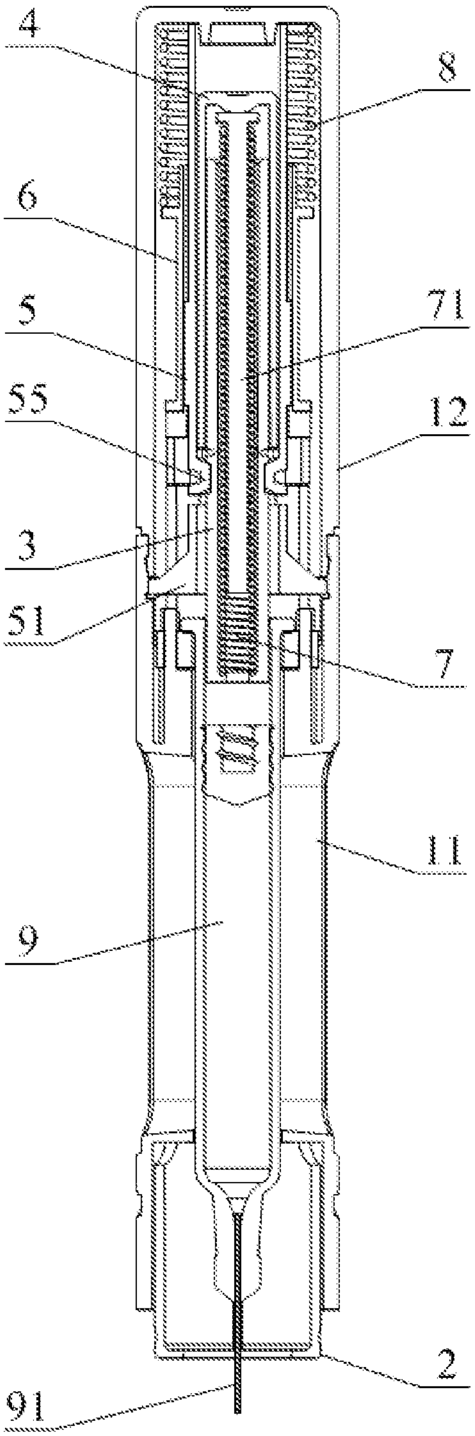
FIG. 37 is a fourth longitudinal sectional diagram of the automatic syringe during use in the specific embodiment of the present application.

During the movement of the release ring 6 towards the rear end of the housing 1, the first clip 55 of the inner tube 5 disengages from the limitation of the inner wall of the release ring 6, thus no longer snap-fitting and limiting the push rod 3. Then, as shown in FIG. 36 and FIG. 37, the push rod 3 slides towards the front end of the syringe 9 under the action of the push rod spring 7, and injects, by pushing the piston 93, the liquid in the syringe 9 into the body through the needle 91, thus achieving automatic injection.

Figure 38:
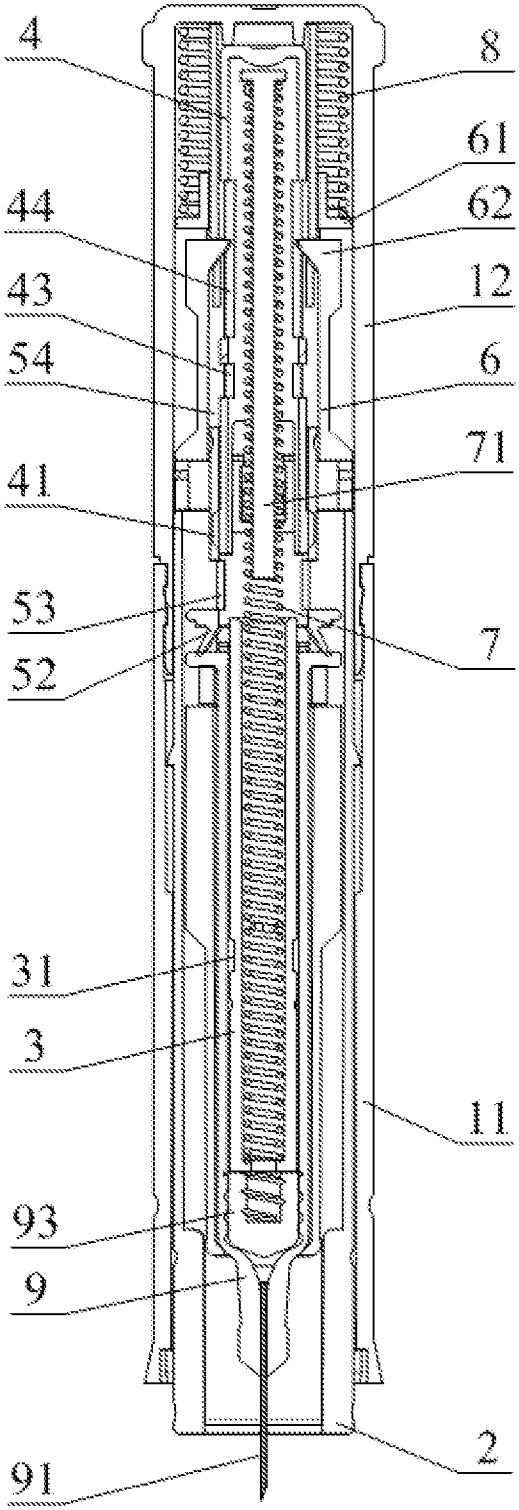
FIG. 38 is a fifth longitudinal sectional diagram of the automatic syringe during use in the specific embodiment of the present application.
Figure 39:
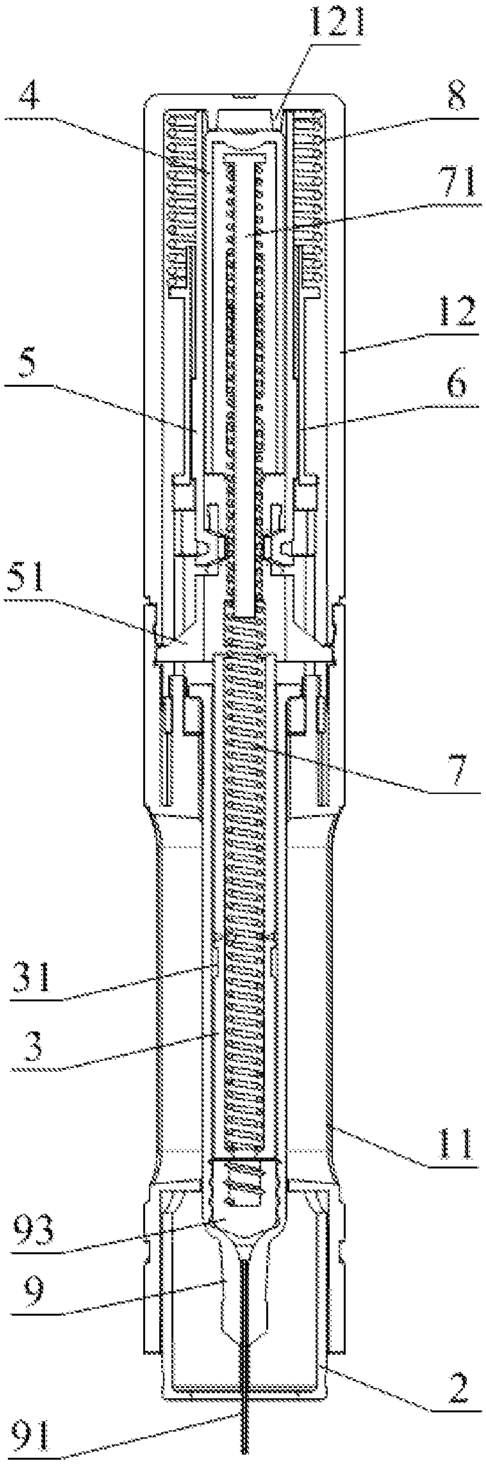
FIG. 39 is a sixth longitudinal sectional diagram of the automatic syringe during use in the specific embodiment of the present application.

In the injection by the push rod 3, the outer wall of the push rod 3 can provide continuous support for the prompting-cylinder protrusion 41, thereby ensuring that the positions of the prompting cylinder 4 and the inner tube 5 are relatively fixed. After the push rod 3 has slid for a preset distance, that is, after the push rod 3 has injected a preset amount of liquid in the syringe 9 into the body, the prompting-cylinder protrusion 41 is no longer supported by the outer wall of the push rod 3, so that the prompting cylinder 4 can slide towards the rear end of the housing 1 under the action of the push rod spring 7. In the process of sliding or after sliding for a certain distance, the prompting cylinder 4 can remind the user that the injection is complete in various ways, such as sounding, lighting, impact, and vibration. In this solution, the prompting cylinder 4 collides with the annular protrusion 121 located on an inner side of the end plate 120 of the rear housing 12 to make a sound to prompt the completion of injection, as shown in FIG. 38 and FIG. 39. The user only needs to pull the needle 91 out of the body to complete the whole injection process.

Figure 40:
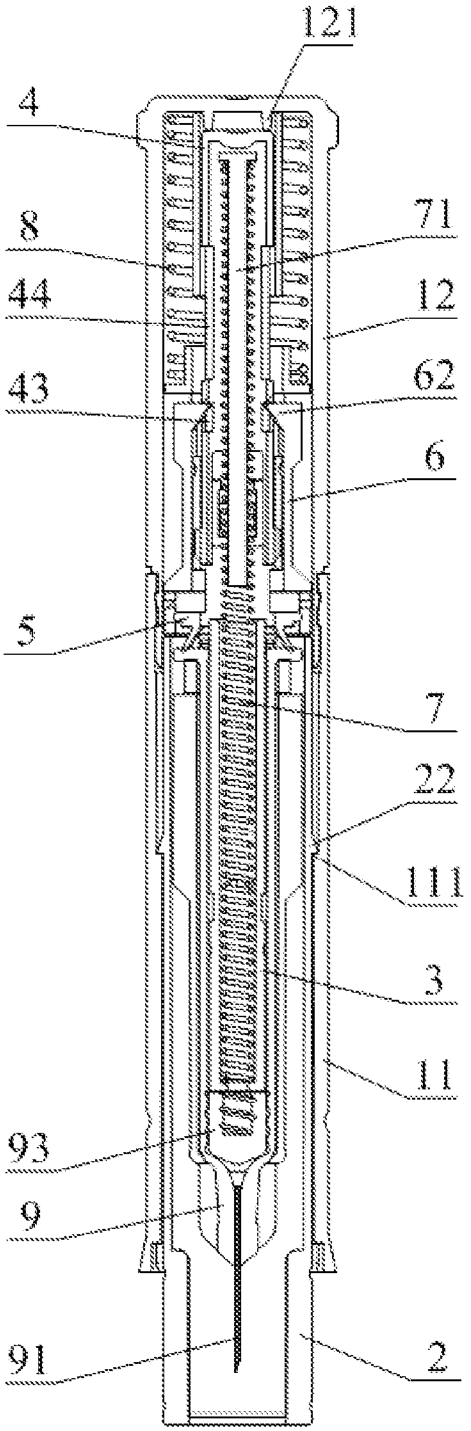
FIG. 40 is a schematic longitudinal sectional diagram of the automatic syringe after use in the specific embodiment of the present application.
Figure 41:
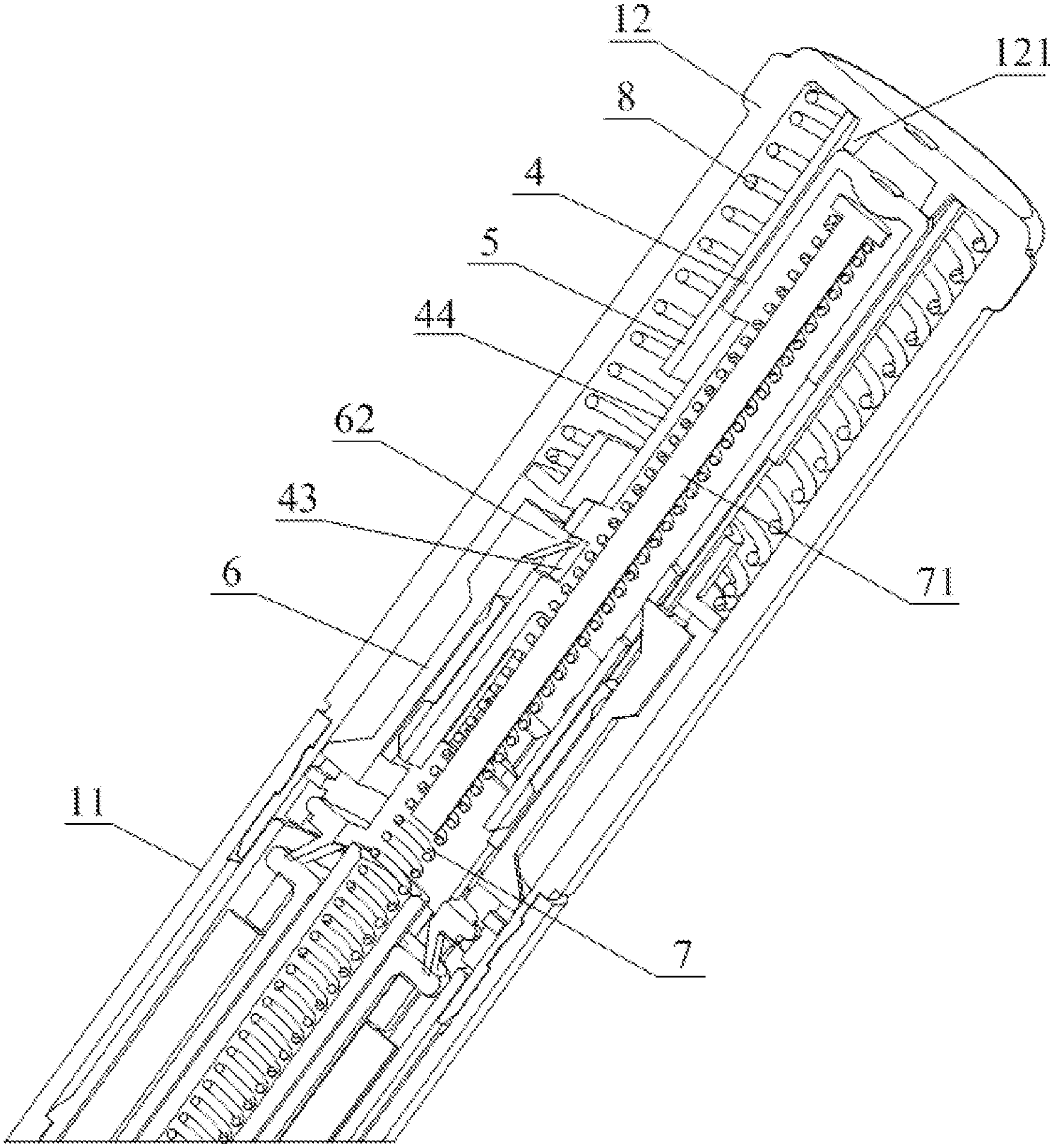
FIG. 41 is an enlarged view of a partial longitudinal section of the automatic syringe after use in the specific embodiment of the present application.

In addition, since the reset spring 8 is compressed when the release ring 6 is pushed towards the rear end, once the front end of the needle guard cover 2 leaves the injection site, the release ring 6 is no longer pushed towards the rear end but is pushed towards the front end by the reset spring 8, thereby forcing the needle guard cover 2 to return to the first limiting step 111 of the front housing 11, as shown in FIG. 40. After the needle guard cover 2 returns to the initial axial position, the axial position of the prompting cylinder 4 has moved towards the rear end of the housing 1 for a certain distance, the second clip 62 of the release ring 6 is fitted into the clip limiting opening 43 of the prompting cylinder 4, so that the prompting cylinder 4 is axially limited by the clip limiting opening 43 and cannot move towards the rear end again, as shown in FIG. 40 and FIG. 41. Therefore, the axial position of the needle guard cover 2 can be fixed and the needle 91 can be prevented from being exposed, that is, the automatic syringe is prevented from being reused, thus ensuring high use safety.

The technical solution of the present application has the following beneficial effects.

1) The automatic syringe provided in this solution can achieve the automatic injection function of the pre-filled syringe through eight components. As compared with the automatic syringe in the conventional technology, the automatic syringe in this solution has a simple structure and fewer parts.
2) In this solution, the automatic injection function can be achieved just by pressing. The mechanism has a simple operation principle and high reliability.
3) The product is easy to assemble, thus reducing the manual assembly cost and improving the product yield.

Based on the above description of the disclosed embodiments, those skilled in the art can implement or deploy the present application. Various modifications to these embodiments are apparent to those skilled in the art. The general principles defined herein may be applied to other embodiments without departing from the spirit or scope of the present application. Therefore, the present application should not be limited to the embodiments disclosed herein, but has the widest scope in accordance to the principle and the novel features disclosed herein.

The invention claimed is:

1. An automatic injector, comprising:

a housing;

a needle guard cover;

a push rod;

a prompting cylinder;
an inner tube;
a release ring;
a driving elastic member; and
a resetting elastic member;

wherein a syringe fixing structure for fixing a pre-filled syringe is arranged in the housing; an opening for a needle to extend out is arranged at a front end of the housing;

the release ring and the needle guard cover are sequentially and slidably arranged on an inner side of the housing from a rear end to the front end of the housing; the needle guard cover is configured to extend out of the front end of the housing and slide towards the rear end relative to the housing to push the release ring; the resetting elastic member is configured to act on the release ring and drive the release ring to push the needle guard cover to slide towards the front end of the housing; the housing is provided with a needle-guard-cover limiting structure for limiting a forward sliding distance of the needle guard cover relative to the housing;

the push rod is slidable in the housing along an axial direction; a front end of the push rod is configured to push a piston in the pre-filled syringe; the driving elastic member is configured to act on the push rod and drive the push rod to slide towards a front end of the pre-filled syringe; a push-rod limiting structure is arranged on an outer circumference of the push rod;

the prompting cylinder is slidably sleeved on the outer circumference of the push rod along the axial direction; the driving elastic member is configured to act on the prompting cylinder and drive the prompting cylinder to slide towards a rear end of the housing; the prompting cylinder is provided with a push-rod-limiting cooperating structure; a prompting-cylinder limiting structure is arranged between the prompting cylinder and the inner tube;

the inner tube is fixed inside the housing and sleeved on an outer circumference of the prompting cylinder; the release ring is slidably sleeved on an outer circumference of the inner tube only along the axial direction; the inner tube is provided with a first clip capable of elastically moving along a radial direction, and the first clip is deviated radially outward under its own elastic force;

the first clip is configured to be deviated radially inward under limiting from an inner wall of the release ring, and be snap-fitted and position-limited with the push-rod limiting structure through the push-rod-limiting cooperating structure; under support of an outer wall of the push rod, the prompting-cylinder limiting structure is configured to limit sliding of the prompting cylinder relative to the inner tube; and after the push rod has slid towards the front end for a preset distance, the prompting-cylinder limiting structure is no longer supported by the push rod; and the inner tube is provided with an inner-tube avoidance slot hole extending along the axial direction, the release ring is provided with a second clip which is in sliding fit with the inner-tube avoidance slot hole and configured to interact with the prompting cylinder; and an outer side of the prompting cylinder is provided with a clip limiting opening used for limiting a movement of the second clip towards the rear end of the housing, and a clip avoidance opening is defined in a side wall of the prompting cylinder and located at a rear end of the clip limiting opening.

2. The automatic injector according to claim 1, wherein a signal structure is arranged at the rear end of the housing and configured to collide and be position-limited with the prompting cylinder.

3. The automatic injector according to claim 2, wherein the signal structure is an end plate fixed at the rear end of the housing.

4. The automatic injector according to claim 1, further comprising a needle cap detachably connected to a front end of the needle guard cover.

5. The automatic injector according to claim 4, wherein a rear end of the needle cap is provided with a claw for catching a rear end of a needle sheath, and the claw is configured to exert a pulling force on the needle sheath towards the front end.

6. The automatic injector according to claim 4, wherein an anti-dropping recess-protrusion engaging structure is arranged between an inner ring of the needle cap and a circumference of the needle guard cover.

7. The automatic injector according to claim 4, wherein a needle-cap limiting structure is arranged between the housing and the needle cap, wherein the needle-cap limiting structure is configured to limit a movement of the needle cap towards the rear end relative to the housing.

8. The automatic injector according to claim 1, wherein the syringe fixing structure is a syringe fixing cylinder fixed on the inner side of the housing, and a front end of the syringe fixing cylinder is provided with a syringe clamping claw for position-limiting and cooperating with a front shoulder of the pre-filled syringe.

9. The automatic injector according to claim 8, wherein a rear end of the syringe fixing cylinder is provided with a support body for position-limiting and cooperating with a rear end flange of the pre-filled syringe, and an elastic cushion block is arranged between the support body and a front end face of the rear end flange of the pre-filled syringe.

10. The automatic injector according to claim 9, wherein a front end of the inner tube abuts against a rear end face of the rear end flange of the pre-filled syringe, and a rear end of the inner tube abuts against the rear end of the housing.

11. The automatic injector according to claim 10, wherein the rear end of the housing is provided with an annular protrusion coaxially cooperating with the rear end of the inner tube; and a rotation limiting structure for preventing the inner tube from rotating is arranged between a side wall of the housing and the inner tube.

12. The automatic injector according to claim 1, wherein the push-rod-limiting cooperating structure is a prompting-cylinder avoidance notch defined in a side wall of the prompting cylinder, and the prompting-cylinder avoidance notch extends along an axial direction of the prompting cylinder.

13. The automatic injector according to claim 1, wherein the prompting-cylinder limiting structure comprises a prompting-cylinder protrusion arranged on an outer wall of the prompting cylinder and an inner-tube clamping hole defined in the inner tube for clamping and limiting the prompting-cylinder protrusion.

14. The automatic injector according to claim 1, wherein the push rod is of a hollow rod-shaped structure, and the driving elastic member is a push rod spring arranged inside the push rod, wherein the push rod spring is compressed between a front end of the push rod and a rear end of the prompting cylinder.

15. The automatic injector according to claim 14, wherein a spring guide rod is slidably arranged in the push rod, and the push rod spring is sleeved on an outer circumference of the spring guide rod.

16. The automatic injector according to claim 1, wherein the resetting elastic member is a reset spring compressed between the release ring and the housing.

17. The automatic injector according to claim 1, wherein the housing comprises a front housing and a rear housing, wherein the front housing is connected to a front end of the rear housing.

18. The automatic injector according to claim 1, wherein the housing and the needle guard cover are each provided with an observation window extending along the axial direction.

19. The automatic injector according to claim 1, wherein the needle-guard-cover limiting structure comprises a first limiting step arranged on an inner wall of the housing and a second limiting step arranged on an outer wall of the needle guard cover.

* * * * *